US011442160B2

(12) United States Patent
Baheti et al.

(10) Patent No.: US 11,442,160 B2
(45) Date of Patent: Sep. 13, 2022

(54) MULTIFUNCTIONAL RADAR SYSTEMS AND METHODS OF OPERATION THEREOF

(71) Applicant: Infineon Technologies AG, Neubiberg (DE)

(72) Inventors: Ashutosh Baheti, Munich (DE); Reinhard-Wolfgang Jungmaier, Aying (DE); Saverio Trotta, Munich (DE); Avik Santra, Munich (DE)

(73) Assignee: INFINEON TECHNOLOGIES AG, Neubiberg (DE)

( * ) Notice: Subject to any disclaimer, the term of this patent is extended or adjusted under 35 U.S.C. 154(b) by 866 days.

(21) Appl. No.: 15/866,194

(22) Filed: Jan. 9, 2018

(65) Prior Publication Data

US 2019/0212436 A1    Jul. 11, 2019

(51) Int. Cl.
*G01S 13/88* (2006.01)
*H01Q 1/22* (2006.01)
(Continued)

(52) U.S. Cl.
CPC ............ *G01S 13/88* (2013.01); *A61B 5/0205* (2013.01); *A61B 5/1126* (2013.01);
(Continued)

(58) Field of Classification Search
CPC .... G01S 13/9011; G01S 13/723; G01S 13/88; G01S 13/4463; G01S 7/415; G01S 13/87;
(Continued)

(56) References Cited

U.S. PATENT DOCUMENTS 10,401,479 B2 *   9/2019   Mabrouk ................ G01S 13/52
10,684,693 B2 *   6/2020   Kletsov .................. G01S 7/2925
(Continued)

FOREIGN PATENT DOCUMENTS

DE      102016210366 B3 *   9/2017   ........... H01Q 21/205
EP          3040736 A1 *    7/2016   ........... H01Q 1/3275

OTHER PUBLICATIONS

Y. -C. Chiu, F. -K. Wang, Y. -R. Chou and T. -S. Horng, "Wearable Doppler radar health monitor with gesture control," 2014 Asia-Pacific Microwave Conference, 2014, pp. 944-946. (Year: 2014).*
(Continued)

*Primary Examiner* — Matthew M Barker
(74) *Attorney, Agent, or Firm* — Slater Matsil, LLP

(57) ABSTRACT

A radar system includes a substrate, a first received antenna, a second receive antenna, and radio frequency (RF) circuitry. The substrate includes a first side and a second side. The first side is opposite the second side. The first receive antenna is disposed at the first side and is configured to receive a first reflected RF signal. The second receive antenna is configured to receive a second reflected RF signal. The RF circuitry is operatively coupled to the first receive antenna and the second receive antenna. The RF circuitry is configured to detect a first object located on the first side of the substrate according to the first reflected RF signal. The RF circuitry is further configured to detect biometric data from a second object located on the second side of the substrate according to the second reflected RF signal.

21 Claims, 15 Drawing Sheets

(51) Int. Cl.
| | |
|---|---|
| *H01Q 25/00* | (2006.01) |
| *A61B 5/11* | (2006.01) |
| *H01Q 1/27* | (2006.01) |
| *G01S 13/72* | (2006.01) |
| *A61B 5/00* | (2006.01) |
| *H01Q 1/52* | (2006.01) |
| *G01S 7/41* | (2006.01) |
| *A61B 5/0205* | (2006.01) |
| *G01S 13/87* | (2006.01) |
| *G01S 7/03* | (2006.01) |
| *H04B 1/44* | (2006.01) |
| *G01S 13/34* | (2006.01) |
| *G01S 13/44* | (2006.01) |
| *G01S 7/02* | (2006.01) |

(52) U.S. Cl.
CPC ............ *A61B 5/6817* (2013.01); *G01S 7/032* (2013.01); *G01S 7/415* (2013.01); *G01S 13/723* (2013.01); *G01S 13/87* (2013.01); *H01Q 1/2283* (2013.01); *H01Q 1/273* (2013.01); *H01Q 1/525* (2013.01); *H01Q 25/005* (2013.01); *H04B 1/44* (2013.01); *G01S 7/028* (2021.05); *G01S 13/34* (2013.01); *G01S 13/4463* (2013.01)

(58) Field of Classification Search
CPC .... G01S 7/032; G01S 13/825; G01S 13/9029; G01S 2007/028; G01S 13/34; G01S 2013/0245; G01S 13/931; G01S 2013/93273; A61B 5/6817; A61B 5/1114; A61B 5/0205; A61B 5/1126; A61B 5/30; H01Q 1/525; H01Q 1/2283; H01Q 25/005; H01Q 9/0457; H01Q 1/273; H04B 1/44
See application file for complete search history.

(56) References Cited

U.S. PATENT DOCUMENTS

| | | | | |
|---|---|---|---|---|
| 10,736,566 | B2* | 8/2020 | Sazonov | A61B 5/6803 |
| 10,757,497 | B2* | 8/2020 | Austen | H04R 1/1016 |
| 2006/0094937 | A1 | 5/2006 | Immoreev et al. | |
| 2008/0077327 | A1* | 3/2008 | Harris | G01S 13/931 |
| | | | | 701/301 |
| 2011/0181510 | A1 | 7/2011 | Hakala et al. | |
| 2012/0116231 | A1 | 5/2012 | Liao et al. | |
| 2013/0050016 | A1* | 2/2013 | Kim | H01L 25/16 |
| | | | | 342/195 |
| 2015/0181840 | A1 | 7/2015 | Tupin, Jr. et al. | |
| 2016/0174842 | A1* | 6/2016 | Hyde | A61B 5/6867 |
| | | | | 342/52 |
| 2016/0249133 | A1 | 8/2016 | Sorensen | |
| 2016/0259037 | A1 | 9/2016 | Molchanov et al. | |
| 2016/0269815 | A1 | 9/2016 | Liao et al. | |
| 2016/0320853 | A1 | 11/2016 | Lien et al. | |
| 2017/0316192 | A1 | 11/2017 | Razouane et al. | |
| 2018/0164429 | A1* | 6/2018 | Tasovac | G01S 13/584 |
| 2018/0273030 | A1* | 9/2018 | Weldon | G01S 17/931 |
| 2018/0353086 | A1* | 12/2018 | Turner | G01S 13/88 |
| 2019/0064344 | A1* | 2/2019 | Turner | A61B 5/6898 |
| 2019/0101636 | A1* | 4/2019 | Trotta | G01S 13/66 |

OTHER PUBLICATIONS

Hsu, Tzu-Wei et al., "Compact 24-GHz Doppler radar module for non-contact human vital-sign detection", 2016 International Symposium on Antennas and Propagation (ISAP), IEICE, Oct. 24, 2016, 2 pages.

* cited by examiner

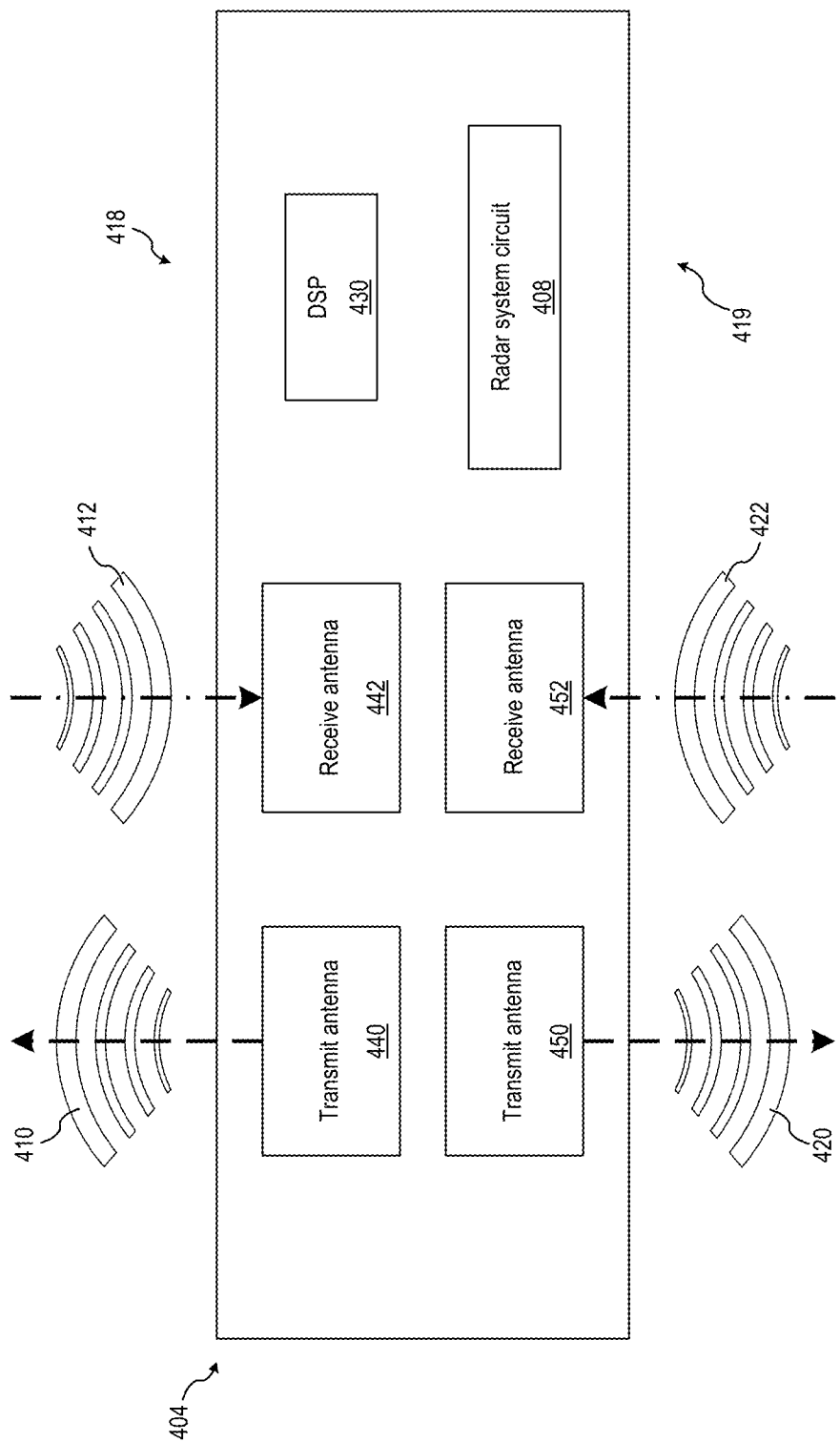

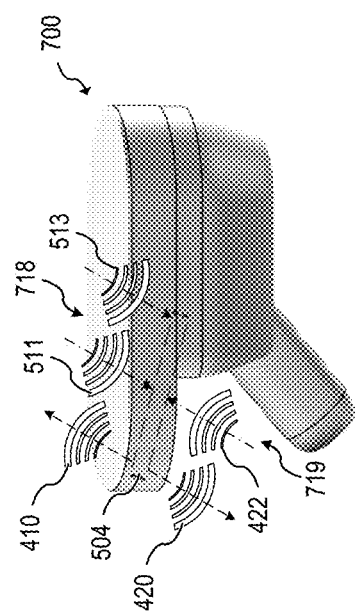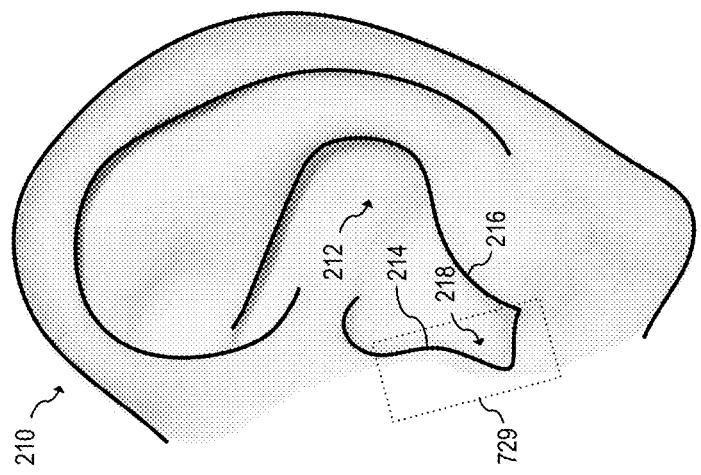
Fig. 7

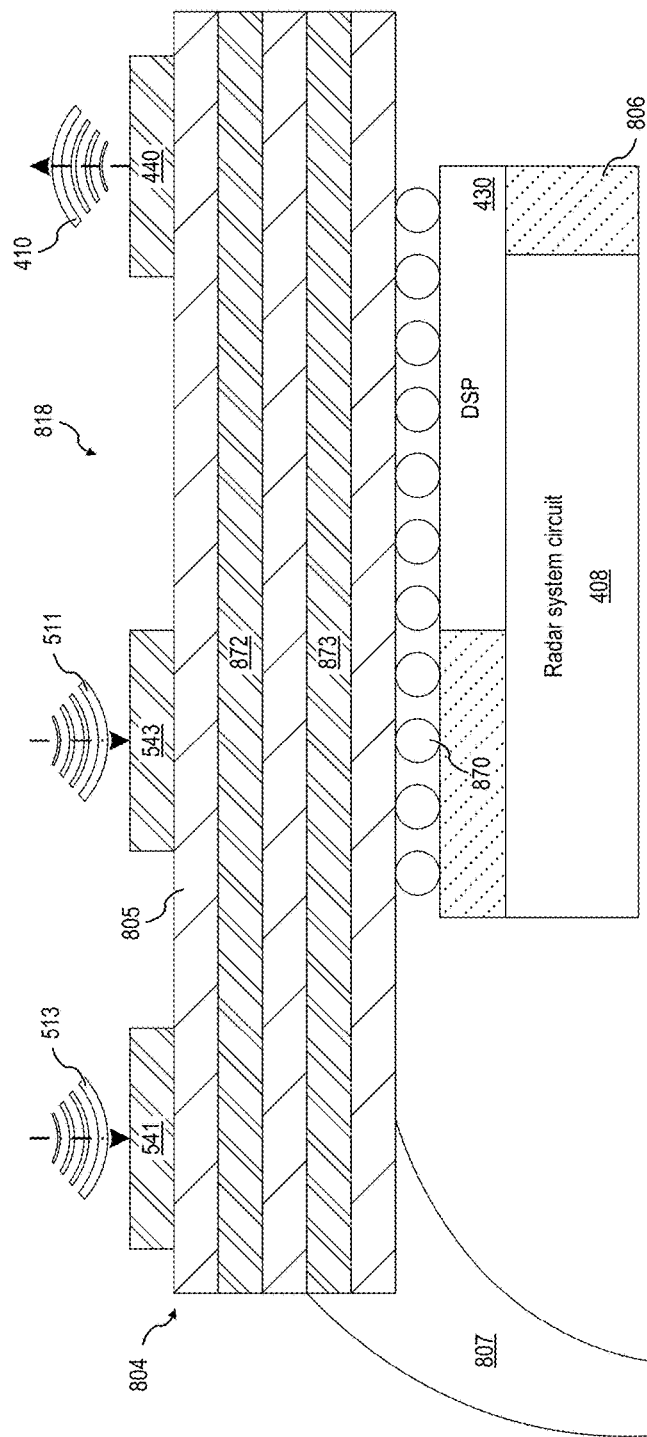
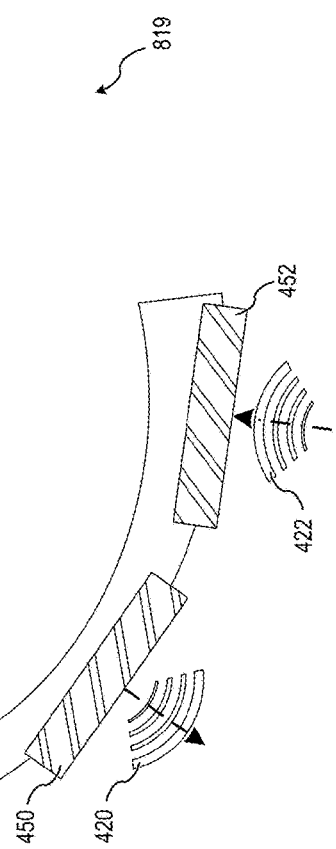
Fig. 8

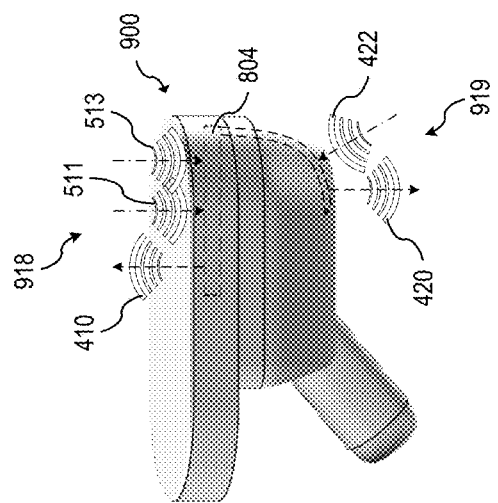
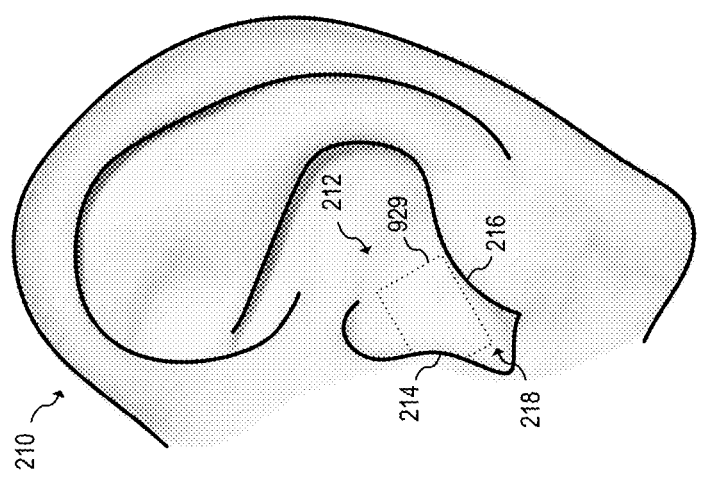
Fig. 9

MULTIFUNCTIONAL RADAR SYSTEMS AND METHODS OF OPERATION THEREOF

TECHNICAL FIELD

The present invention relates generally to a multifunctional radar system, and, in particular embodiments, to structures of multifunctional radar systems and methods of operation thereof.

BACKGROUND

Portable devices such as tablets, smart phones, smart watches, and smart earphones have become popular recently due to the rapid advancement in low-cost semiconductor technologies. Portable devices may need to perform a variety of functions such as presence detection, gesture sensing, and biometric measurements, as examples. Various implementations may be used to accomplish this including capacitive sensors and infrared sensors among others. However such sensor modules may increase the size of the portable device. Therefore, portable devices which incorporate alternative means performing functions such as presence detection, gesture sensing, and biometric measurements may be desirable to decrease device size, decrease cost, and improve functionality.

SUMMARY

In accordance with an embodiment of the invention, a radar system includes a substrate, a first received antenna, a second receive antenna, and radio frequency (RF) circuitry. The substrate includes a first side and a second side. The first side is opposite the second side. The first receive antenna is disposed at the first side and is configured to receive a first reflected RF signal. The second receive antenna is configured to receive a second reflected RF signal. The RF circuitry is operatively coupled to the first receive antenna and the second receive antenna. The RF circuitry is configured to detect a first object located on the first side of the substrate according to the first reflected RF signal. The RF circuitry is further configured to detect biometric data from a second object located on the second side of the substrate according to the second reflected RF signal.

In accordance with another embodiment of the invention, a method of operating a radar system includes receiving a first reflected RF signal. The first reflected RF signal is received by a first receive antenna located at a first side of a substrate. The method further includes detecting a first object located on the first side of the substrate according to the first reflected RF signal. The first objected is detected by the RF circuitry. The RF circuitry is operatively coupled to the first receive antenna. The method also includes receiving a second reflected RF signal. The second reflected RF signal is received by a second receive antenna operatively coupled to the RF circuitry. The method still further includes detecting biometric data from a second object located on a second side of the substrate according to the second reflected RF signal. The biometric data is detected by the RF circuitry. The second side is opposite of the first side.

In accordance with still another embodiment of the invention, an earphone device includes a housing, an acoustic transducer, and a radar system. The housing includes a top region and a bottom region. The acoustic transducer is disposed in the bottom region of the housing. The radar system is disposed in the top region of the housing. The radar system includes a first side and an opposite second side. The radar system is configured to detect a first object located on the first side of the radar system. The radar system is further configured to detect biometric data from a second object located on the second side of the radar system.

In accordance with yet another embodiment of the invention, a method of operating an earphone device includes detecting motion of a first object. The motion is detected at a first side of the earphone device. The method further includes interpreting the motion of the first object as a gesture. The method also includes controlling the earphone device according to the gesture. The method still further includes detecting biometric data of a second object. The biometric data is detected at a second side of the earphone device. The second side is opposite the first side.

In accordance with still yet another embodiment of the invention, a method includes checking an enrollment database for template data, determining that template data has been received from the enrollment database, and updating the enrollment database using heart rate signature data.

BRIEF DESCRIPTION OF THE DRAWINGS

For a more complete understanding of the present invention, and the advantages thereof, reference is now made to the following descriptions taken in conjunction with the accompanying drawings, in which:

FIG. 4 illustrates an example radar system including a radar system circuit, digital signal processor, front side transmit and receive antennas, and back side transmit and receive antennas in accordance with an embodiment of the invention;

FIG. 7 illustrates an example earphone in relation to an ear where the earphone includes a radar system including two front side receive antennas, a front side transmit antenna, and back side transmit and receive antennas in accordance with an embodiment of the invention;

FIG. 8 illustrates an example radar system including two front side receive antennas and a front side transmit antenna attached to a first substrate, a radar system circuit and a digital signal processor attached to a second substrate, and back side transmit and receive antennas attached to a flexible substrate in accordance with an embodiment of the invention;

FIG. 9 illustrates an example earphone in relation to an ear where the earphone includes a radar system including two front side receive antennas and a front side transmit antenna attached to a first substrate and back side transmit and receive antennas attached to a flexible substrate in accordance with an embodiment of the invention;

Corresponding numerals and symbols in the different figures generally refer to corresponding parts unless otherwise indicated. The figures are drawn to clearly illustrate the relevant aspects of the embodiments and are not necessarily drawn to scale. The edges of features drawn in the figures do not necessarily indicate the termination of the extent of the feature.

DETAILED DESCRIPTION OF ILLUSTRATIVE EMBODIMENTS

The making and using of various embodiments are discussed in detail below. It should be appreciated, however, that the various embodiments described herein are applicable in a wide variety of specific contexts. The specific embodiments discussed are merely illustrative of specific ways to make and use various embodiments, and should not be construed in a limited scope.

Portable devices may utilize antenna elements for beamforming, transmit diversity and MIMO configurations, and as radar sensors that can detect user motions (known as gesture sensors). Gesture sensors may be configured in a portable device as an interface to control functionality of the device as well as to gather information about objects in the area around the portable device. Radar sensors may also be configured to acquire biometric information from a user or other living organism in vicinity of the portable device.

In various embodiments, a radar-based gesture detection system is used to directly control a device such as a computer, a smartphone, or a tablet computer, or to control a remote device such as a vehicle, an electronic system within a building, or a home appliance. For example, when the remote device is a car, an embodiment gesture detection system allows a human actor to control various operations of the car from outside the car.

Figure 1A:
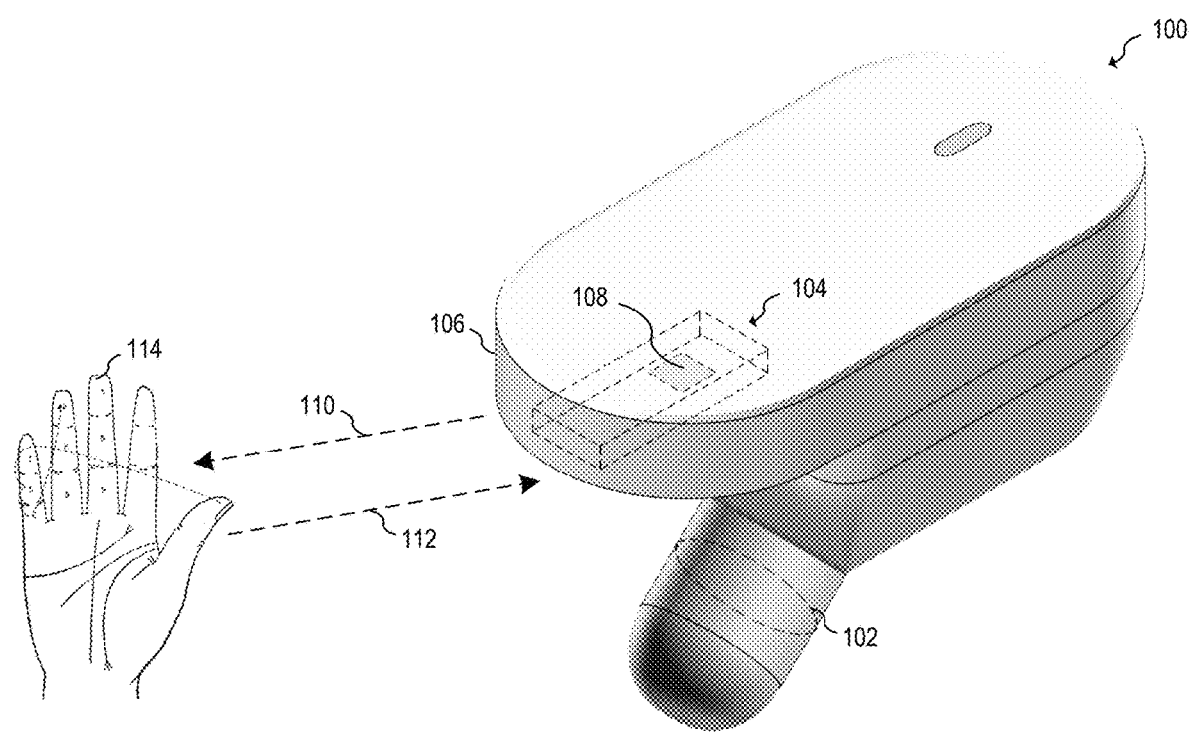
FIG. 1A illustrates an example radar system application in which a portable device is controlled using various hand gestures.

FIG. 1A illustrates an example radar system application in which a portable device 100 is controlled using various hand gestures. As shown, portable device 100 may be a smart earphone and includes a speaker element 102 configured to output audible sound to the ear of a user. During operation, a sensor region 104 transmits RF signals no to target 114, which may be a human hand, and receives reflected RF signals 112 that are reflected by target 114. These reflected RF signals 112 are processed by the radar system to determine the position and motion of target 114 and/or to determine whether target 114 is providing a particular gesture. In some embodiments, sensor region 104 may include a radar system circuit 108 that is disposed within a sensor region 104. At least a portion of sensor region 104 is transparent or partially transparent to RF signals transmitted and received by radar system circuit 108. It should be appreciated that radar system circuit 108 may also be disposed in other locations within portable device 100.

In alternative embodiments, radar system circuit 108 may be embedded within other devices including, but not limited to, car keys, smart watches, tablet computers, audio/visual equipment, kitchen appliances, heating, ventilation, and air conditioning (HVAC) controls, and automobiles. In some applications, such as automotive applications, radar system circuit 108 may be embedded within a mobile device such as a car key, smart watch, or smart phone, which in turn communicates with a remote device to be controlled, such as an automobile or kitchen appliance. The data transfer between the mobile device and remote device could include any of a wide variety of communications technologies, including, e.g., Bluetooth, vehicle-to-everything (V2X), etc.

Figure 1B:
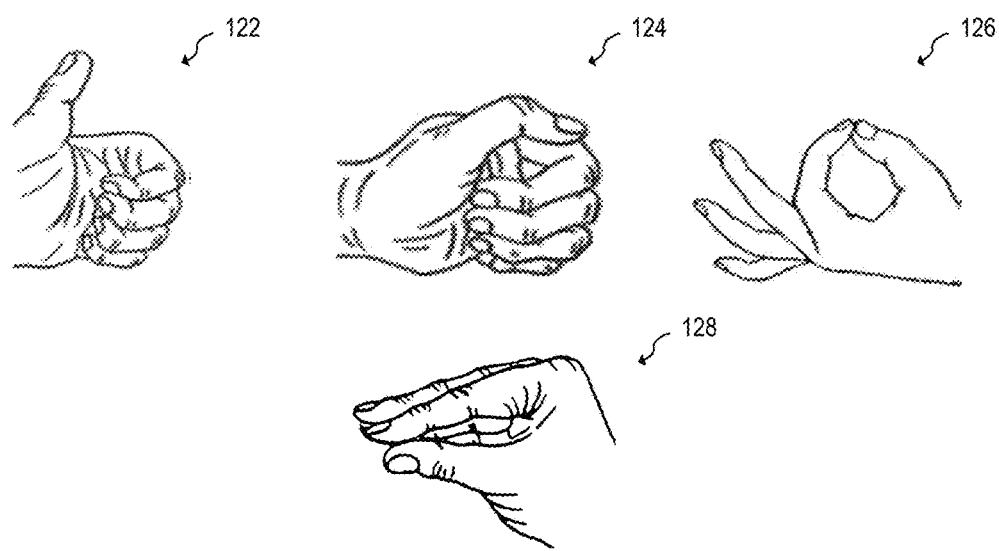
FIG. 1B illustrates various example hand gestures that may be used to control a portable device.

Example hand gestures shown in FIG. 1B may include, for example, a "thumbs-up" gesture 122, a "closed fist" gesture 124, a "thumb-to-finger" gesture 126, or a "button press" gesture 128. Each of these example gestures could be used to control the functionality of portable device 100 or some other device or system. For example, "thumbs-up" gesture 122 could be used to open a portable device application, "closed fist" gesture 124 could be used to close the portable device application, "thumb-to-finger" gesture 126 in conjunction with motion between the thumb and index finger may be used to virtually rotate the images on the display of portable device 100, and "button press" gesture 128 could be used to start and stop a stopwatch feature of portable device 100. In various embodiments, recognized gestures may be static or dynamic. Static gestures may be made by holding a hand in a fixed position such as the gestures 122, 124 and 128, and dynamic gestures may be made by moving the hand or a portion of the hand, such as moving the index finger with respect to the thumb such as with gesture 126. It should be understood that the above-mentioned gestures are just a few examples of many possible gestures that may be recognized by embodiment radar systems.

Figure 1C:
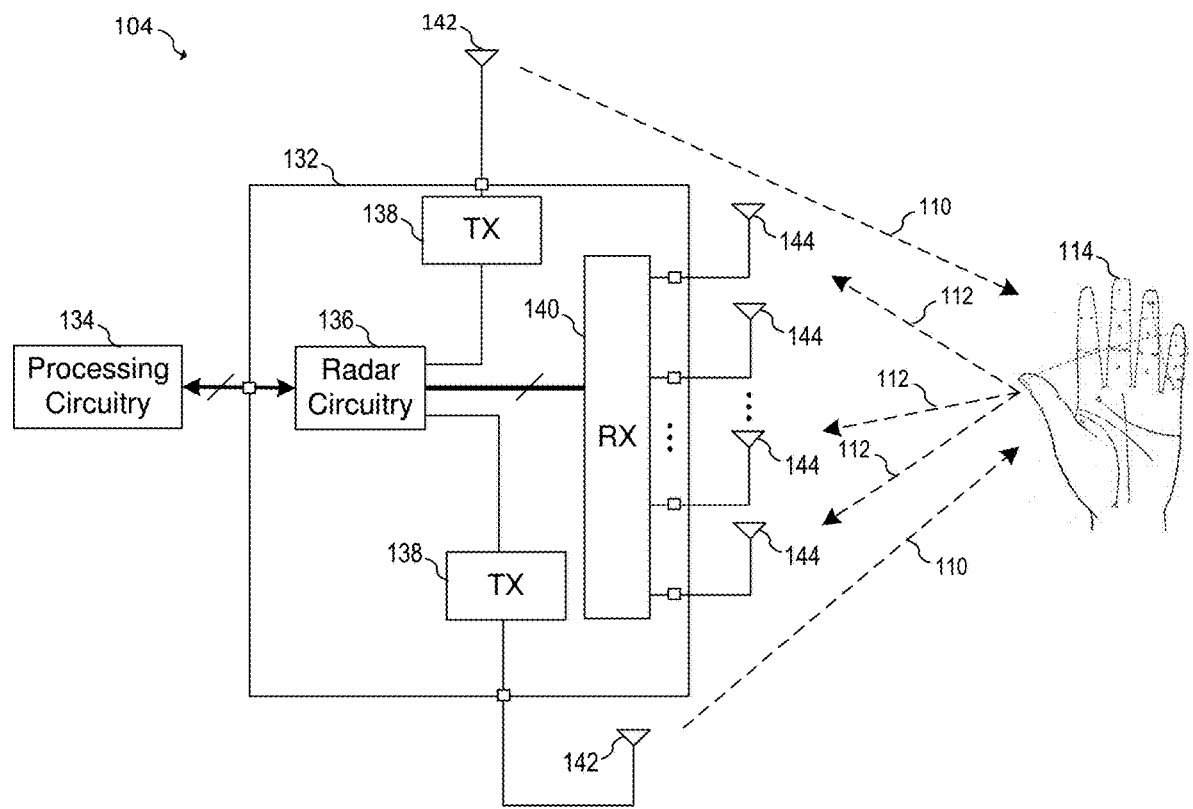
FIG. 1C illustrates a block diagram of a sensor region that includes an RF front end circuit and processing circuitry.

FIG. 1C illustrates a block diagram of sensor region 104 that includes radar front-end circuit 132 and processing circuitry 134. During operation, positions and gestures of target 114 may be detected by the sensor region 104. For example, a gesture of two fingers tapping each other could be interpreted as a "button press," or a gesture of a rotating thumb and finger may be interpreted as turning a dial. While target 114 is depicted in FIG. 1C as being a hand, sensor region 104 may also be configured to determine gestures and positions of other types of targets such as a human body, machinery and other types of animate or inanimate objects. Sensor region 104 may be implemented, for example, using a two-dimensional millimeter-wave (MMW) phase-array radar that measures the position and relative speed of target 114. The MMW phase-array radar transmits and receives signals in the 50 GHz to 80 GHz range. Alternatively, frequencies outside of this range may also be used. In some embodiments, radar front-end circuit 132 operates as a frequency modulated continuous wave (FMCW) radar sensor having multiple transmit and receive channels.

Radar front-end circuit 132 transmits and receives radio signals for detecting target 114 in three-dimensional space. For example, radar front-end circuit 132 transmits an incident RF signal and receives an RF signal that is a reflection of the incident RF signal from target 114. The received reflected RF signal is downconverted by radar front-end circuit 132 to determine beat frequency signals. These beat frequency signals may be used to determine information such as the location, speed, angle, etc., of target 114 in three-dimensional space.

In various embodiments, radar front-end circuit 132 is configured to transmit incident RF signals toward target 114 via transmit antennas 142 and to receive reflected RF signals from target 114 via receive antennas 144. Radar front-end circuit 132 includes transmitter front-end circuits 138 coupled to transmit antennas 142 and receiver front-end circuit 140 coupled to receive antennas 144.

During operation, transmitter front-end circuits 138 may transmit RF signals toward target 114 one at a time or simultaneously. While two transmitter front-end circuits 138 are depicted in FIG. 1C, it should be appreciated that radar front-end circuit 132 may include fewer or greater than two transmitter front-end circuits 138. Each transmitter front-end circuit 138 includes circuitry configured to produce the incident RF signals. Such circuitry may include, for example, RF oscillators, upconverting mixers, RF amplifiers, variable gain amplifiers, filters, transformers, power splitters, and other types of circuits.

Receiver front-end circuit 140 receives and processes the reflected RF signals from target 114. As shown in FIG. 1C, receiver front-end circuit 140 is configured to be coupled to four receive antennas 144, which may be configured as a 2×2 antenna array. In alternative embodiments, receiver front-end circuit 140 may be configured to be coupled to greater or fewer than four antennas, with the resulting antenna array being of various n×m dimensions depending on the specific embodiment and its specifications. Receiver front-end circuit 140 may include, for example, RF oscillators, upconverting mixers, RF amplifiers, variable gain amplifiers, filters, transformers, power combiners and other types of circuits.

Radar circuitry 136 provides signals to be transmitted to transmitter front-end circuits 138, receives signals from receiver front-end circuit 140, and may be configured to control the operation of radar front-end circuit 132. In some embodiments, radar circuitry 136 includes, but is not limited to, frequency synthesis circuitry, upconversion and downconversion circuitry, variable gain amplifiers, analog-to-digital converters, digital-to-analog converters, digital signal processing circuitry for baseband signals, bias generation circuits, and voltage regulators.

Radar circuitry 136 may receive a baseband radar signal from processing circuitry 134 and control a frequency of an RF oscillator based on the received baseband signal. In some embodiments, this received baseband signal may represent a FMCW frequency chirp to be transmitted. Radar circuitry 136 may adjust the frequency of the RF oscillator by applying a signal proportional to the received baseband signal to a frequency control input of a phase locked loop. Alternatively, the baseband signal received from processing circuitry 134 may be upconverted using one or more mixers. Radar circuitry 136 may transmit and digitize baseband signals via a digital bus (e.g., a USB bus), transmit and receive analog signals via an analog signal path, and/or transmit and/or receive a combination of analog and digital signals to and from processing circuitry 134.

Processing circuitry 134 acquires baseband signals provided by radar circuitry 136 and performs one or more signal processing steps to evaluate them. In an embodiment, processing circuitry 134 acquires a baseband signal that represents the beat frequency signals. The signal processing steps may include performing a fast Fourier transform (FFT), a short-time Fourier transform (STFT), target classification, machine learning, and the like. Results of the signal processing steps are used to determine and perform an action on the device, such as portable device 100 of FIG. 1A. In addition to processing the acquired baseband signals, processing circuitry 134 may also control aspects of radar front-end circuit 132, such as the transmissions produced by radar front-end circuit 132.

The various components of sensor region 104 may be partitioned in various ways. For example, radar front-end circuit 132 may be implemented on one or more RF integrated circuits (RFICs), antennas 142 and 144 may be disposed on a circuit board, and processing circuitry 134 may be implemented using a processor, a microprocessor, a digital signal processor and/or a custom logic circuit disposed on one or more integrated circuits/semiconductor substrates. Processing circuitry 134 may include a processor that executes instructions stored in a non-transitory memory to perform the functions of processing circuitry 134. In some embodiments, however, all or part of the functionality of processing circuitry 134 may be incorporated on the same integrated circuit/semiconductor substrate on which radar front-end circuit 132 is disposed.

In some embodiments, some or all portions of radar front-end circuit 132 may be implemented in a package that contains transmit antennas 142, receive antennas 144, transmitter front-end circuits 138, receiver front-end circuit 140, and/or radar circuitry 136. In some embodiments, radar front-end circuit 132 may be implemented as one or more integrated circuits disposed on a circuit board, and transmit antennas 142 and receive antennas 144 may be implemented on the circuit board adjacent to the integrated circuits. In some embodiments, transmitter front-end circuits 138, receiver front-end circuit 140, and radar circuitry 136 are formed on a same radar front-end integrated circuit (IC) die. Transmit antennas 142 and receive antennas 144 may be part of the radar front-end IC die, or may be separate antennas over or adjacent to the radar front-end IC die. The radar front-end IC die may further include conductive layers, such as redistribution layers (RDLs), used for routing and/or for the implementation of various passive or active devices of radar front-end circuit 132. In an embodiment, transmit antennas 142 and receive antennas 144 may be implemented using the RDLs of the radar front-end IC die.

Figure 1D:
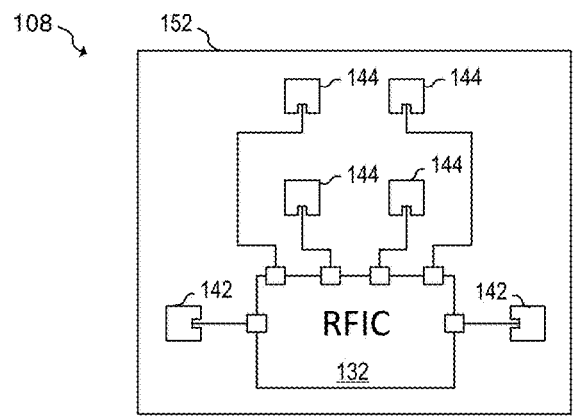
FIG. 1D illustrates a plan view of a radar system circuit that includes a RF front end circuit implemented as a radio frequency integrated circuit.

FIG. 1D illustrates a plan view of radar system circuit 108 that includes radar front-end circuit 132 implemented as an RFIC coupled to transmit antennas 142 and receive antennas 144 implemented as patch antennas disposed on or within substrate 152. In some embodiments, substrate 152 may be implemented using a circuit board on which radar front-end circuit 132 is disposed and on which transmit antennas 142 and receive antennas 144 are implemented using conductive layers of the circuit board. Alternatively, substrate 152 represents a wafer substrate on which one or more RDLs are disposed and on which transmit antennas 142 and receive antennas 144 are implemented using conductive layers on the one or more RDLs. It should be appreciated that the implementation of FIG. 1D is just one of many ways that embodiment radar systems may be implemented.

In addition to gesture sensing, a radar system may also provide biometric information about a user or other living organism in range of the radar system. For example, a radar system may be configured to sense the heart rate of a living organism such as a user. In some cases a radar system may be configured to sense a heart rate signature of a living organism which may provide additional information including identification information.

In various applications, an electronic device may benefit from radar implementations that combine multiple radar functions into a single device. For example, the multiple radar functions may include presence detection, gesture sensing, and heart rate sensing. A multifunctional radar system may be used to implement a presence detection and gesture sensing application at an exposed exterior side of the radar system, and to implement a heart rate sensing application at an interior side of the radar system.

Radar functions of a multifunctional radar system may also include material identification, blood pressure tracking, collision avoidance, object identification and activity identification, audio source tracking, contact tracking, and biometric identification. For example, an earphone may use the front-facing radar of a multifunctional radar system for gesture sensing while using the back-facing radar for heart rate monitoring and contact tracking to know if a user is wearing the earphones or if the earphones are on a charger.

In various embodiments, a radar system includes a substrate with a first side and an opposite second side. In some cases, the first side may be considered a front side and the second side may be considered a back side of the radar system. One or more receive antennas are configured to receive a first reflected RF signal at the front side of the radar system. One or more additional receive antennas are configured to receive a second reflected RF signal at the back side of the radar system. RF circuitry is operatively coupled to the one or more receive antennas and the one or more additional receive antennas. The RF circuitry is configured to detect a first object on the front side of the radar system according to the first reflected RF signal. The RF circuitry is further configured to detect biometric data from a second object on the back side of the radar system according to the second reflected RF signal.

The RF circuitry may be further configured to detect motion of the first object. The radar system may also include a digital signal processor (DSP) that is configured to process signals received from the RF circuitry. The DSP may also be configured to interpret motion of the first object as a gesture for controlling the radar system. The DSP may be configured to interpret biometric information of the second object as a heart rate signature of a living organism such as a user. The heart rate signature may be used to identify and/or authenticate a user.

Transmitter front-end circuitry may also be included in the radar system. The transmitter front-end circuitry may be configured to transmit a first transmitted RF signal in a first direction away from the front side of the radar system. The transmitter front-end circuitry may also be configured to transmit a second transmitted RF signal in a second direction away from the back side of the radar system. The first transmitted RF signal may generate the first reflected RF signal after contacting an object that is at least partially opaque to RF signals. Similarly, the second transmitted RF signal may generate the second reflected RF signal.

Radar systems including multiple radar functions may advantageously provide similar capabilities as other non-radar modules while occupying a smaller volume of space within an electronic device. For example, a conventional portable device may include multiple capacitive sensors, ultrasound, and infrared sensors in addition to a pulse oximetry sensor which may include infrared and photodetector sensors. In contrast, a multifunctional radar system may include a single radar module that is smaller than the combined total volume of the sensors in a conventional portable device with similar functionality.

An additional benefit of radar systems including multiple radar functions may also be that the performance of the functions may be increased through implementation using radar when compared to the corresponding functions implemented without radar in a conventional portable device. For example, radar implemented gesture sensors may have increased resolution and support multiple targets simultaneously. As another example, radar implemented heart rate sensors may be unaffected by ambient light and temperature. In comparison, a pulse oximetry sensor may be dependent on the external environmental effects such as light, temperature, mechanical instability, as examples.

Another possible advantage of radar systems that include multiple radar functions is to enable the multiple radar functions by including a single MMW radar system in a portable device. The MMW radar system may be formed as a single integrated package as well as on a printed circuit board (PCB) which may advantageously allow flexibility in design. The radar system may include an RF front-end, a baseband processor, and a small DSP. For example, multiple application scenarios may be accomplished by implementing a dual-sided mm-wave radar system including multiple radar functions into an earphone device, headphone device, or headset device while simultaneously decreasing the size of the device.

Embodiments provided below describe various structures and methods of operating a radar system, and in particular, radar systems that include multiple radar functions. The following description describes the embodiments. Two embodiment earphones that each include a radar system are described using FIGS. 2, 3A, and 3B. Several embodiment radar systems are described using FIGS. 4, 5, 6A, and 6B. Another embodiment earphone including a radar system is described using FIG. 7. Another embodiment radar system is described using FIG. 8. Yet another embodiment earphone including a radar system is described using FIG. 9. Embodiment left and right earphones and a table of embodiment gestures with associated functions are described using FIG. 10. Various embodiment methods of operating a radar system are described using FIGS. 11-14.

Figure 2:
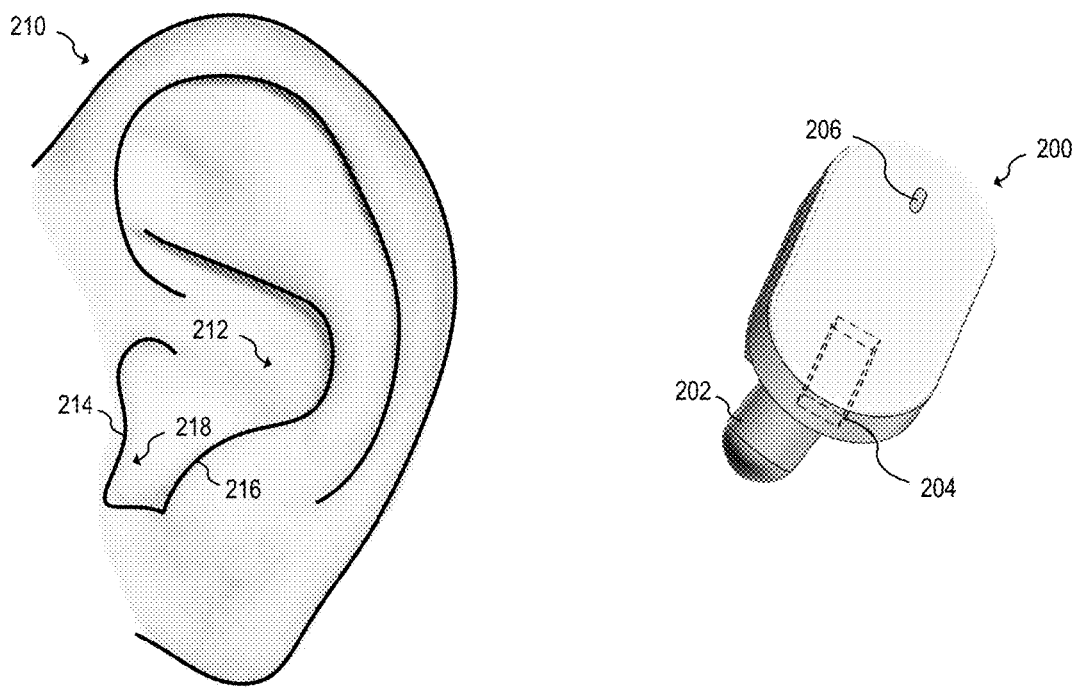
FIG. 2 illustrates an example earphone in relation to an ear where the earphone includes a radar system in accordance with embodiments of the invention.

FIG. 2 illustrates an example earphone in relation to an ear where the earphone includes a radar system in accordance with embodiments of the invention.

Referring to FIG. 2, an example earphone 200 includes a radar system 204, an acoustic transducer 202, and an indicator light 206. In various embodiments, radar system 204 may be implemented using similar circuitry as radar system 104 as previously described. The radar system 204 is configured to provide multiple radar functions. For example, radar system 204 may be configured to detect the presence of nearby objects as well as detect biometric information from a nearby living organism. In one embodiment, radar system 204 is configured to detect the presence of nearby objects, detect gestures of a user in order to control the earphone 200, and detect the heart rate of a user.

Other possible radar functions may be included in radar system 204. For example, object motion tracking, material identification, object identification and activity identification, audio source tracking, contact tracking, collision avoidance, blood pressure tracking, heart rate tracking, heart rate signature detection, biometric identification and authentication, and others may be included in radar system 204. In some cases a heart rate may also be referred to as a pulse.

The acoustic transducer 202 may be any suitable type of acoustic transducer such as a speaker, microspeaker, microspeaker array, and the like. The indicator light 206 may indicate various information related to earphone 200 such as a powered-on state, a charging state, and other particular operating states or modes, the detection of the presence of an object, detection of the presence of a gesture, and others.

Earphone 200 may be configured to interface with an ear 210 of a user so that acoustic transducer 202 can provide audible sound to the user. The ear 210 of a user may include the anatomical structures of the concha 212, tragus 214, anti-tragus 216, and ear canal 218. In one embodiment, earphone 200 is configured to fit into the ear canal 218 of the user while partially or entirely covering the concha 212, tragus 214, and anti-tragus 216. In some cases, an earphone 200 that is configured to fit into the ear canal 218 of a user may be implemented as an earbud. In other embodiments, earphone 200 may be implemented as an over-ear earphone. In various alternative embodiments, earphone 200 may be implemented as a headphone earpiece which may be part of a pair of headphones or a headset.

Radar system 204 may provide one set of radar functions on a side of the earphone 200 that faces away from the user while providing a second set of radar functions on another side of the earphone 200 that faces toward the user. In some cases, the side facing away from the user may be thought of as the front side of the earphone 200 while the side facing toward the user may be thought of as the back side. For example, in one embodiment, earphone 200 may use the front-facing radar of a dual-sided radar system for object presence detection and gesture sensing while using the back-facing radar for heart rate monitoring and contact tracking to know if a user is wearing the earphone 200 or if earphone 200 is on a charging base.

The earphone 200 may be implemented as part of a pair of earphones. For example, earphone 200 may be a left earphone configured to interface with the left ear of a user while a right earphone is configured to interface with the right ear of a user. In some embodiments, earphone 200 is implemented as a left earphone with multiple radar functions while a right earphone is also implemented with multiple radar functions. In one embodiment, the radar functionality of the left earphone is similar or identical to the radar functionality of the right earphone. In other embodiments, the radar functionality of the left earphone may be different than the radar functionality of the right earphone. In still other embodiments, only one of the two earphones may be implemented with radar functionality.

One or more surfaces of earphone 200 may be configured to overlap or directly contact specific anatomical structures of the ear 210 of a user. For example, the concha 212 may be a useful region for detecting biometric information of a user such as heart rate. In one embodiment, earphone 200 directly contacts the concha 212 of the ear 210 of a user. In another embodiment, earphone 200 overlaps the tragus 214 of the ear 210 of a user. The tragus 214 may also be convenient as a region for biometric information of a user. Earphone 200 may be configured to utilize the concha 212, tragus 214 and anti-tragus 216 to maintain an optimal operational position over or within ear 210.

Figure 3A:
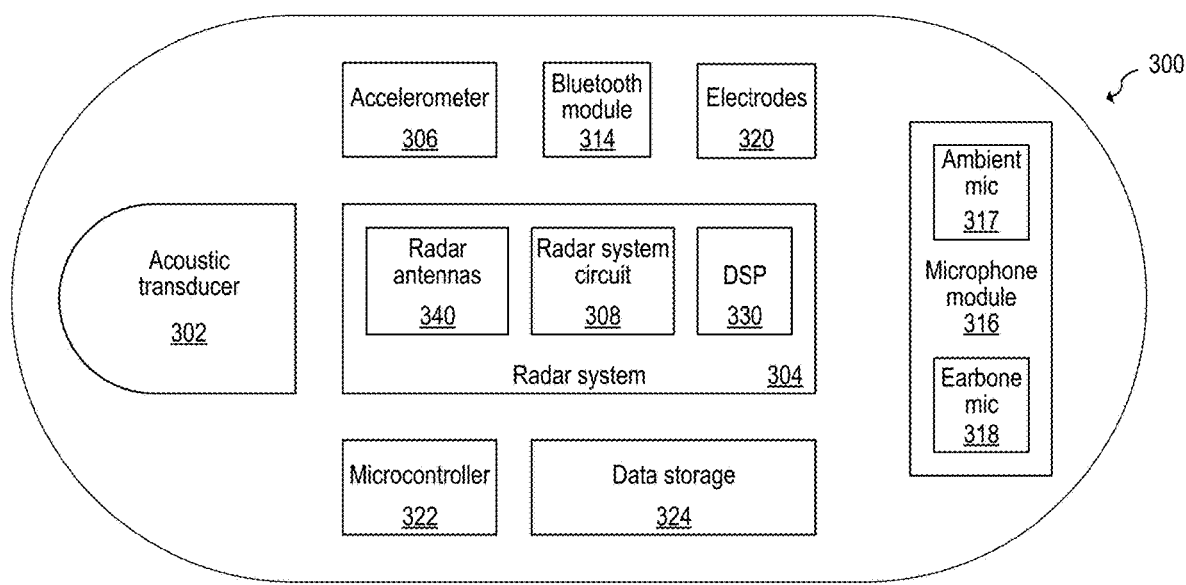
FIG. 3A illustrates a block diagram of an example earphone including a radar system and FIG. 3B illustrates a schematic diagram of the example earphone in accordance with an embodiment of the invention.
Figure 3B:
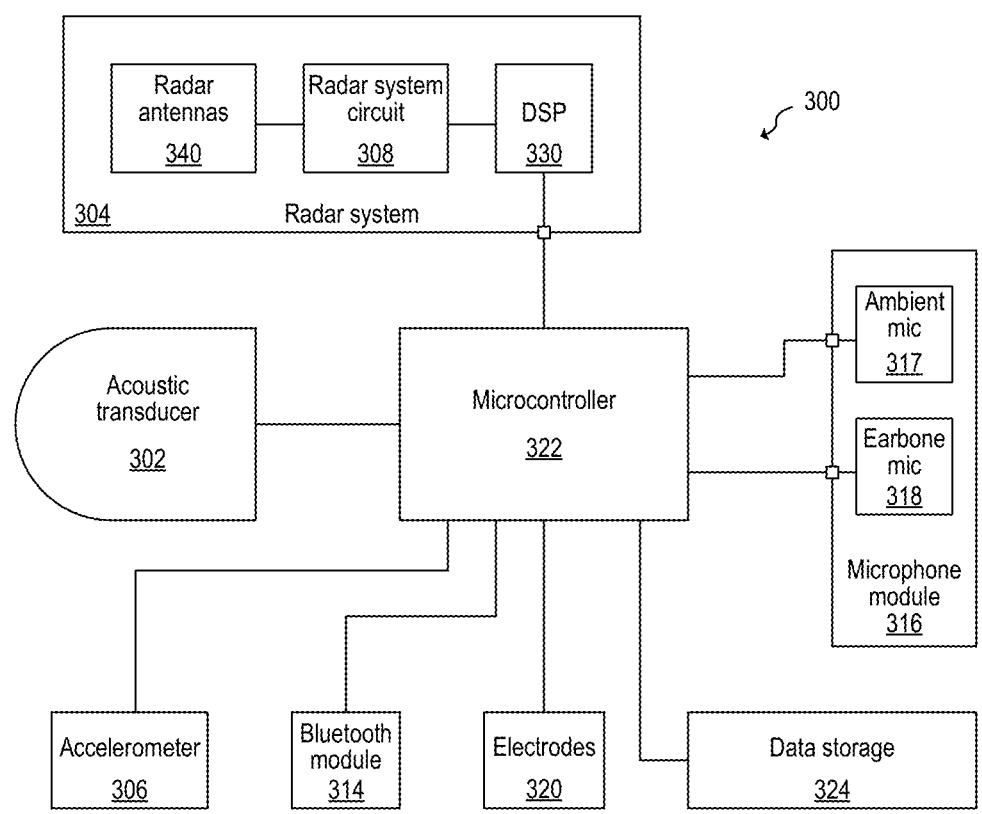

FIG. 3A illustrates a block diagram of an example earphone including a radar system and FIG. 3B illustrates a schematic diagram of the example earphone in accordance with an embodiment of the invention.

Referring to FIGS. 3A and 3B, an earphone 300 includes an acoustic transducer 302 and a radar system 304. Earphone 300, acoustic transducer 302, and radar system 304 may be specific implementations of earphone 200, acoustic transducer 202, and radar system 204 as previously described. Radar system 304 includes a radar system circuit 308, a DSP 330, and radar antennas 340. The radar system circuit 308 may include transmitter front-end circuitry, receiver front-end circuitry, RF circuitry, radar circuitry, processing circuitry, and the like. Additionally, earphone 300 optionally includes an accelerometer 306, a Bluetooth module 314, electrodes 320, a microphone module 316, a microcontroller 322, and data storage 324.

The microcontroller 322 may be included to control various functions of earphone 300. Data storage 324 may also be included to allow local storage of media, settings, documents, and the like. Various components of earphone 300 may be connected to microcontroller 322. For example, as shown in FIG. 3B, acoustic transducer 302, radar system 304, accelerometer 306, Bluetooth module 314, electrodes 320, microphone module 316, and data storage 324 may be operatively coupled to microcontroller 322. Radar system 304 may be coupled to microcontroller 322 using a connection to DSP 330. Additionally, DSP 330 may be coupled to radar system circuit 308 and may perform baseband processing functions.

Earphone 300 may be an example of a smart earphone device utilizing several modules to provide many different functions. For example, Bluetooth module 314 may allow the earphone 300 to pair with an external device that contains audio to enable a user to hear the audio. Additionally, Bluetooth module 314 may also serve to connect earphone 300 to other devices to enable data connections and/or control connections. Accelerometer 306 may be optionally included to track the motion of a user. Possible applications include step counting and head tracking.

Electrodes 320 may be configured to measure electrical signals within a user. For example, electrodes 320 may include one or more of an electroencephalography (EEG) sensor for measuring electrical signals within the brain, an electromyography (EMG) sensor for measuring electrical signals within muscles, and an electrocardiography (ECG) sensor for measuring electrical activity of the heart. An EEG sensor may be used as a brain interface while EMG and ECG sensors may be used to monitor craniofacial and heart muscles respectively.

The microphone module 316 may include one or more microphones. For example, an earbone microphone 318 may be included to detect speech from the user while one or more ambient microphones 317 may be included to provide noise cancellation and/or three-dimensional ambient awareness functionality. The microcontroller 322 may have individual connections to each of the microphones in microphone module 316 such as ambient microphone 317 and earbone microphone 318.

Various components of earphone 300 have been described above as being independent components or part of a larger module. However, the invention is not limited to any particular arrangement of components within earphone 300. For example, earbone microphone 318 and ambient microphones 317 may be implemented as two or more separate components within earphone 300. Similarly, radar system 304 may be implemented as a fully integrated module or may include one or more components attached to a one or more printed circuit boards. The various components of earphone 300 are illustrated as functional blocks. Accordingly, the locations, orientations, and sizes of the various components as illustrated in FIGS. 3A and 3B are not necessarily indicative of the locations, orientations, and sizes of components when implemented in actual earphone devices.

FIG. 4 illustrates an example radar system including a radar system circuit, digital signal processor, front side transmit and receive antennas, and back side transmit and receive antennas in accordance with an embodiment of the invention.

Referring to FIG. 4, a radar system 404 includes a front side transmit antenna 440 and a front side receive antenna 442 configured to transmit a front side transmitted RF signal 410 and receive a front side reflected RF signal 412 at a front side 418 of radar system 404. A back side transmit antenna 450 and a back side receive antenna 452 are also included in radar system 404 and are configured to transmit a back side transmitted RF signal 420 and receive a back side reflected RF signal 422 at a back side 419 of radar system 404. In various embodiments, the radar system 404 may be a specific implementation of radar system 204 and may include circuitry similar to radar system 104 as previously described.

Front side transmitted RF signal 410 may generate front side reflected RF signal 412 by being wholly or partially reflected by objects on the front side 418 of radar system 404. Similarly, back side transmitted RF signal 420 be wholly or partially reflected by objects on the back side 419 of radar system 404 to generate back side reflected RF signal 422. Any of the antennas included in radar system 404 may be implemented using one or more antenna elements. For example, front side receive antenna 442 may be implemented as two side-by-side antenna patches in one embodiment. In another embodiment, front side receive antenna may be implemented as an array of antenna elements.

Still referring to FIG. 4, the radar system 404 also includes a radar system circuit 408 and a DSP 430. The radar system circuit 408 is operatively coupled to DSP 430, front side transmit antenna 440, front side receive antenna 442, back side transmit antenna 450, and back side receive antenna 452. Radar system circuit 408 may include transmitter front-end circuitry operatively coupled to front side transmit antenna 440 and back side transmit antenna 450 and receiver front-end circuitry coupled to front side receive antenna 442 and back side receive antenna 452. The transmitter front-end circuitry may be configured to transmit the front side transmitted RF signal 410 in a direction away from radar system 404 on the front side 418. The transmitted front-end circuitry may also be configured to transmit the back side transmitted RF signal 420 in a direction away from radar system 404 on the back side 419.

Radar system circuit 408 may also include RF circuitry, radar circuitry, processing circuitry, and the like. The DSP 330 may be configured to process signals received from RF circuitry included in radar system circuit 408. RF circuitry may be configured to detect various events in the region surrounding radar system 404. For example, radar system circuit 408 may include RF circuitry configured to enable multiple radar functions of radar system 404. For example, RF circuitry included in radar system circuit 408 may be configured to detect an object located on the front side 418 of radar system 404 according to the front side reflected RF signal 412 received by front side receive antenna 442. In some cases, this radar functionality may be expanded so that the RF circuitry is further configured to detect two-dimensional or three-dimensional motion of the object located on the front side 418 of radar system 404.

RF circuitry included in radar system circuit 408 may also be configured to detect biometric data from an object located on the back side 419 of radar system 404 according to the back side reflected RF signal 422 received by bask side receive antenna 452. For example, the biometric data may include vital information of a user such as a vital Doppler signal. In one embodiment, the biometric data is heart rate data. The heart rate data may include a heart rate and/or heart rate signature. Biometric data such as heart rate data may be used by radar system 404 to monitor vital signs of a user and/or to authenticate a user of a device including the radar system 404.

Radar system 404 may be included in an electronic device. The electronic device may be a portable device in some embodiments. In one embodiment, the electronic device including radar system 404 is an earphone device. In other embodiments the electronic device including radar system 404 is a headphone device, headset device, or earbud device. Other types of electronic device that may implement radar system 404 include a tablet, laptop, or desktop computer, a smartphone, smartwatch, or other smart device, an internet of things (IoT) device, a vehicle, an electronic system within a building, a home appliance, as well as others.

Figure 5:
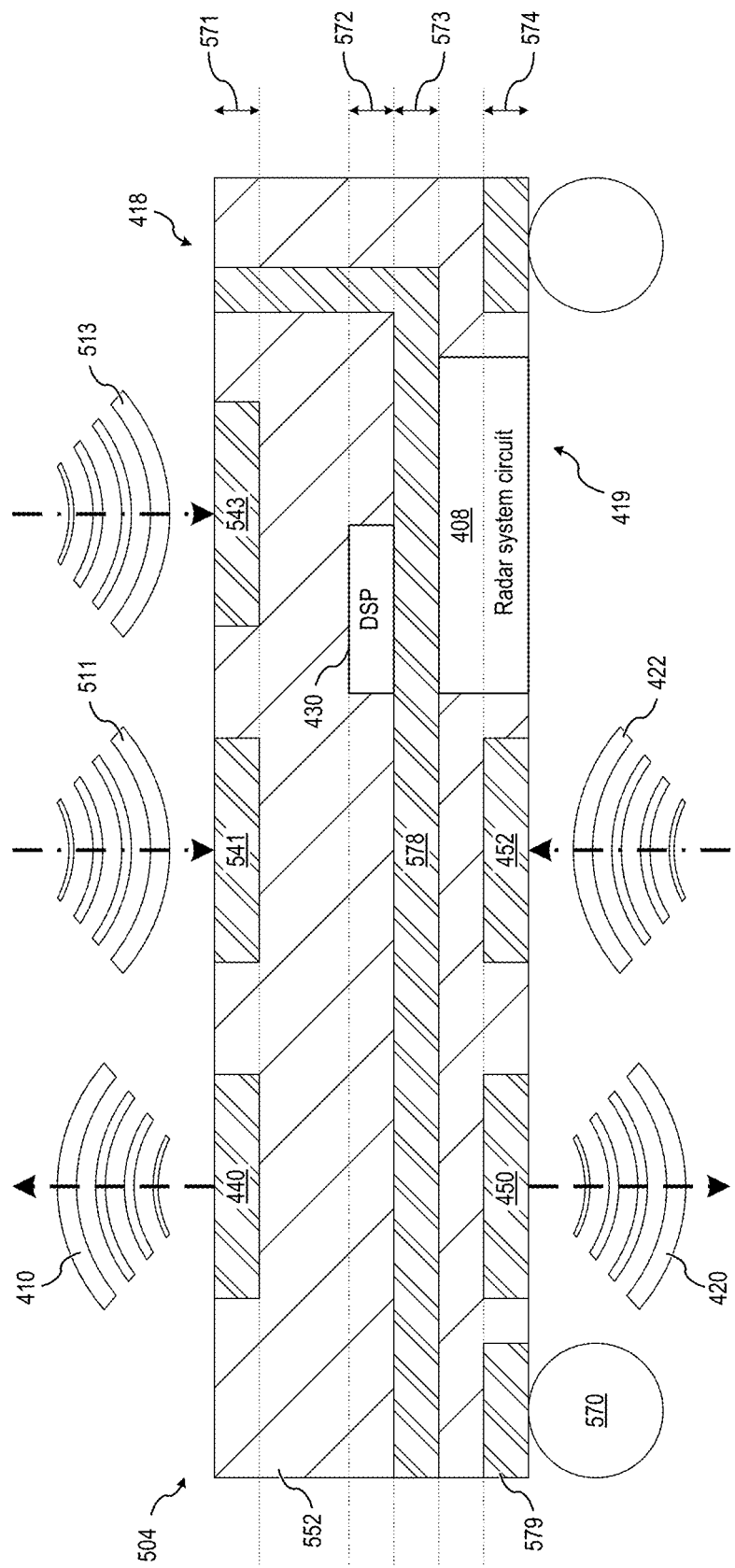
FIG. 5 illustrates an example radar system including a radar system circuit, digital signal processor, and front side and back side antennas within a substrate in accordance with an embodiment of the invention.

FIG. 5 illustrates an example radar system including a radar system circuit, digital signal processor, and front side and back side antennas within a substrate in accordance with an embodiment of the invention.

Referring to FIG. 5, an example radar system 504 is shown which includes multiple antennas attached to a substrate 552 and implemented using four conductive layers. Substrate 552 may be any suitable substrate. For example, substrate 552 may be similar to substrate 152 as previously described. Radar system 504 may be a specific implementation of a radar system as previously described. For example, radar system 504 may be a specific implementation of radar system 404 as previously described.

Radar system 504 includes a front side transmit antenna 440, a first front side receive antenna 541, and a second front side receive antenna 543 implemented in a first conductive layer 571 and attached to substrate 552 on a front side 418 of the radar system 504. The first front side receive antenna 541 and the second front side receive antenna 543 may be a specific implementation of the front side receive antenna 442 as previously described and may be configured to track two-dimensional motion of an object located on the front side 418 of the radar system 504.

Radar system 504 may also include a DSP 430, ground plane region 578, and a radar system circuit 408. The DSP 430 may be implemented in a second conductive layer 572 within substrate 552 and located above ground plane region 578. The ground plane region 578 may be implemented in a third conductive layer 573 and may be configured to shield the antennas at the front side 418 of the radar system 504 from antennas at an opposite back side 419 of the radar system 504. The radar system circuit 408 may be located below ground plane region 578 within substrate 552.

The respective locations of DSP 430 and radar system circuit 408 in the radar system 504 as shown in FIG. 5 are provided as an example and not intended to be limiting. In other implementations DSP 430 and radar system circuit 408 may be implemented at other locations within substrate 552 or be attached to any surface of substrate 552. In some embodiments, one or both of DSP 430 and radar system circuit 408 may be omitted or implemented separately from radar system 504.

Still referring to FIG. 5, radar system 504 also includes a back side transmit antenna 450 and a back side receive antenna 452 implemented in a fourth conductive layer 574. Interconnects 579 may also be implemented in the fourth conductive layer 574. Interconnects 579 may include an interface for connecting to solder balls 570. For example, the interface may be solder pads.

Various transmission lines, interconnects, contact pads, and redistribution lines may be included in any of the conductive layers described herein. For example, front side transmit antenna 440 may be fed directly using a transmission line in the first conductive layer 571 which may be coupled to the radar system circuit 408 using vias or other suitable means. Alternatively, front side transmit antenna 440 may be fed indirectly from a transmission line in another layer such as second conductive layer 572. Similar transmission lines and interconnects may exist to couple the other antennas in radar system 504 to the radar system circuit 408.

The conductive layers described herein include a conductive material and may include a metal in various embodiments. For example, each conductive layer may include one or more of copper (Cu), silver (Ag), gold (Au), aluminum (Al), tungsten (W), platinum (Pt), and palladium (Pd), for example. In some applications, conductive layers may include other conductive materials such as graphene, conductive ceramics, polysilicon, and others. Other suitable conductive materials may also be apparent to those of ordinary skill in the art.

Front side transmit antenna 440, back side transmit antenna 450, and back side receive antenna 452 may be configured to transmit/receive front side transmitted RF signal 410, back side transmitted RF signal 420, and back side reflected RF signal 422 as previously described. Similarly, the first front side receive antenna 541 and the second front side receive antennas 543 may be configured to receive a first front side reflected RF signal 511 and a second front side reflected RF signal 513 generated by front side transmitted RF signal 410.

The first front side reflected RF signal 511 and the second front side reflected RF signal 513 may be generated when front side transmitted RF signal 410 reflects off an object located at a distance on the front side 418 of the radar system 504. Each of the front side reflected RF signals may have different properties as determined by the radar system circuit 408 coupled to first front side receive antenna 541 and second front side receive antenna 543. For example, comparison of phase information included in the front side reflected RF signals may allow the radar system 504 to track the movement of an object located at a distance on the front side 418 of radar system 504 and moving in a direction parallel to a front side surface of substrate 552.

Figures 6A, 6B:
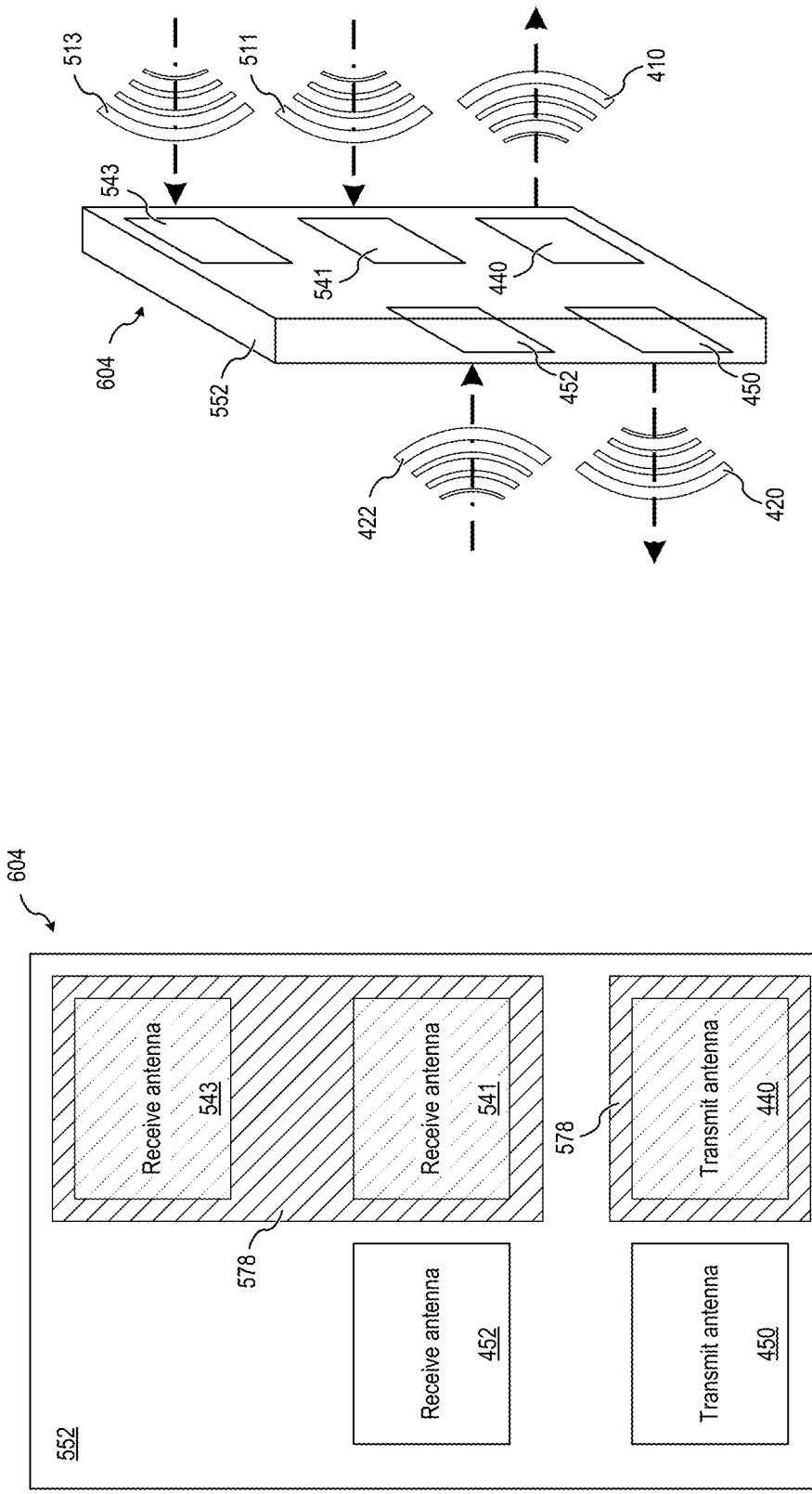
FIG. 6A illustrates a front view of an example radar system including two front side receive antennas, a front side transmit antenna, and back side transmit and receive antennas
FIG. 6B illustrates a three-dimensional view of the example radar system in accordance with an embodiment of the invention.

FIG. 6A illustrates a front view of an example radar system including two front side receive antennas, a front side transmit antenna, and back side transmit and receive antennas and FIG. 6B illustrates a three-dimensional view of the example radar system in accordance with an embodiment of the invention. The example radar system illustrated in FIGS. 6A and 6B may be a specific implementation of other example radar systems as described in previous embodiments such as in reference to FIGS. 1A-1D and 2-5, for example.

Referring to FIGS. 6A and 6B, a top view and a three-dimensional view of a radar system 604 is shown which includes front side transmit antenna 440 and back side transmit antenna 450 disposed on a substrate 552 and configured to transmit a front side transmitted RF signal 410 and a back side transmitted RF signal 420 respectively. In this embodiment, two separate antennas are used to transmit RF signals propagating away from radar system 604 on both a front side and an opposing back side of the radar system 604. However, other configurations are possible. For example, an omnidirectional transmit antenna may be included in radar system 604 configured to transmit both front side transmitted RF signal 410 and back side transmitted RF signal 420.

The radar system 604 further includes a first front side receive antenna 541, a second front side receive antenna 543, and a back side receive antenna 452 disposed on the substrate 552 and configured to receive a first front side reflected RF signal 511, a second front side reflected RF signal 513, and a back side reflected RF signal 422 respectively. In other embodiments, the number of front side and/or back side receive antennas may be changed in order to enable specific functionality on one or both sides of radar system 604. The reflected RF signals may be generated when transmitted RF signals reflect off of objects located at a distance from radar system 604.

In various embodiments, some or all of the antennas included in radar system 604 are implemented as directional antennas. In some embodiments, the antennas of radar system 604 are planar antennas. In one embodiment, the antennas included in radar system 604 are implemented as patch antennas. However, the antennas of radar system 604 may be implemented as any type of suitable antenna including, but not limited to, a tapered slot antenna (TSA), a Vivaldi antenna, a log periodic dipole antenna (LPDA), a quasi-Yagi antenna, a leaky wave antenna (LWA), or the like. Any suitable configuration may be chosen for the antennas including patch, slot, ring, spiral, bow-tie configurations, or any other shape. In some embodiments, the antennas of radar system 604 include an electrically conductive material. In one embodiment, the electrically conductive material includes copper (Cu).

The radar system 604 may also optionally include one or more ground plane regions 578 disposed within the substrate 552 and configured to electromagnetically isolate one or more antennas from one another during operation. For example, as shown in FIG. 6A, ground plane regions 578 may be disposed beneath the front side antennas. The ground plane regions 578 may be configured to prevent electromagnetic radiation such as RF signals generated by the front side antennas from reaching the back side antennas and vice versa. More or fewer ground plane regions may be included in radar system 604. Ground plane regions may be included within substrate 552 or may be disposed on an outer surface of substrate 552. In various embodiments, ground plane regions 578 include a conductive material. In one embodiment, the ground plane regions 578 include copper (Cu).

FIG. 7 illustrates an example earphone in relation to an ear where the earphone includes a radar system including two front side receive antennas, a front side transmit antenna, and back side transmit and receive antennas in accordance with an embodiment of the invention. The example earphone and radar system may be specific implementations of earphones and radar systems as previously described in other embodiments such as in reference to FIGS. 1A-1D, 2-5, 6A, and 6B.

Referring to FIG. 7, an example earphone 700 includes a radar system 504 configured to transmit a front side transmitted RF signal 410 and receive a first front side reflected RF signal 511 and a second front side reflected RF signal 513 at a front side 718 of earphone 700. Earphone 700 is further configured to transmit a back side transmitted RF signal 420 and receive a back side reflected RF signal 422 at a back side 719 of earphone 700. All similarly numbered elements are as previously described.

Earphone 700 is configured to interface with an ear 210 such that audible sound may be supplied to a user. The ear 210 includes typical anatomical structures such as concha 212, tragus 214, anti-tragus 216, and an ear canal 218. Additionally, earphone 700 may be configured to track the motion of objects located on the front side 718 of the earphone 700 to enable control of the earphone 700 using gesture sensing. In one embodiment, the front side 718 of earphone 700 is facing away from a user when the earphone 700 is positioned in the ear 210. In this orientation, earphone 700 may be able to detect gestures from the user and interpret them as input for control of earphone 700.

The earphone 700 may also be configured to detect biometric measurements at the back side 719 of the earphone 700. For example, in various embodiments, the back side 719 of earphone 700 is overlapping a biometric sensing region 729 when the earphone 700 is positioned in the ear 210. In one embodiment, a surface of the back side 719 is in direct contact with the user in the biometric sensing region 729. Alternatively, earphone 700 may be positioned such that area of earphone 700 that overlaps with biometric sensing region 729 includes the radar antennas configured to enable biometric measurements such as heart rate monitoring.

FIG. 8 illustrates an example radar system including two front side receive antennas and a front side transmit antenna attached to a first substrate, a radar system circuit and a digital signal processor attached to a second substrate, and back side transmit and receive antennas attached to a flexible substrate in accordance with an embodiment of the invention. The example radar system of FIG. 8 may be a specific implementation of other radar systems of other embodiments such as any of the radar systems of FIGS. 1A-1D and 2-4.

Referring to FIG. 8, an example radar system 804 includes three front side antennas and two back side antennas similar to previous embodiments. However, in contrast to previous embodiments, the front side antennas of radar system 804 are attached to a first substrate 805 at a front side 818 of radar system 804 while the back side antennas are attached to a flexible substrate 807 at a back side 819 of radar system 804. Additionally, a radar system circuit 408 and a DSP 430 are included within a second substrate 806 which is physically and electrically coupled to the first substrate 805 using solder balls 870.

In various embodiments, the first substrate 805 is a multilayer circuit board and is a multilayer PCB in one embodiment. For example, radar system 804 may include a first conductive layer 872 and a second conductive layer 873 disposed within the first substrate 805. The first conductive layer 872 may be configured as a ground plane and the second conductive layer may include transmission lines and interconnects to enable operational coupling of the front side and/or back side antennas to the radar system circuit 408 and DSP 430.

The second substrate 806 may be an IC chip that includes radar system circuit 408 and DSP 430. For example, in one embodiment, second substrate 806 is a system on chip (SoC) including radar system circuit 408 and DSP 430. The SoC may also include other components such as microcontrollers, memory blocks, external interfaces, voltage regulators, and power management circuits. In other embodiments, second substrate 806 may be implemented using a system in package (SiP) architecture.

Flexible substrate 807 is configured to enable back side transmit antenna 450 and back side receive antenna 452 to be positioned in various locations on the back side of the radar system 804. For example, flexible substrate 807 may be a flexible PCB including transmission lines and/or interconnects that operationally couple the back side antennas to the radar system circuit 408. The back side antennas may be electrically or electromagnetically connected to radar system circuit 408.

FIG. 9 illustrates an example earphone in relation to an ear where the earphone includes a radar system including two front side receive antennas and a front side transmit antenna attached to a first substrate and back side transmit and receive antennas attached to a flexible substrate in accordance with an embodiment of the invention. The example earphone and radar system may be specific implementations of earphones and radar systems as previously described in other embodiments such as in reference to FIGS. 1A-1D, 2-4, and 8.

Referring to FIG. 9, an example earphone 900 includes a radar system 804 configured to transmit a front side transmitted RF signal 410 and receive a first front side reflected RF signal 511 and a second front side reflected RF signal 513 at a front side 918 of earphone 900. Earphone 900 is further configured to transmit a back side transmitted RF signal 420 and receive a back side reflected RF signal 422 at a back side 919 of earphone 900. All similarly numbered elements are as previously described.

As in previously embodiments, earphone 900 is configured to interface with an ear 210 and may be configured to perform multiple radar functions such as tracking the motion of objects for gesture sensing at the exposed front side 918 of earphone 900 as well as detecting biometric measurements on the back side 919 of earphone 900. In contrast to previous embodiments, earphone 900 includes a radar system 804 that includes a flexible substrate configured such that back side antennas overlap a biometric sensing region 929 of the concha 212. In one embodiment, a surface of the back side 919 is in direct contact with the biometric sensing region 929.

Earphone 900 may be advantageously constructed to place back side antennas of radar system 804 near biometric sensing region 929. For example, biometric sensing region 929 may include arteries which facilitate improved accuracy when detecting biometric measurements. Back side antennas attached to a flexible substrate of radar system 804 may be positioned within earphone 900 so that the back side antennas are in close proximity to arteries or other important anatomical structures in biometric sensing region 929. The location of biometric sensing region 929 is given merely as one possible configuration. In other embodiments, biometric sensing region 929 may be at a different location of ear 210.

Figure 10:
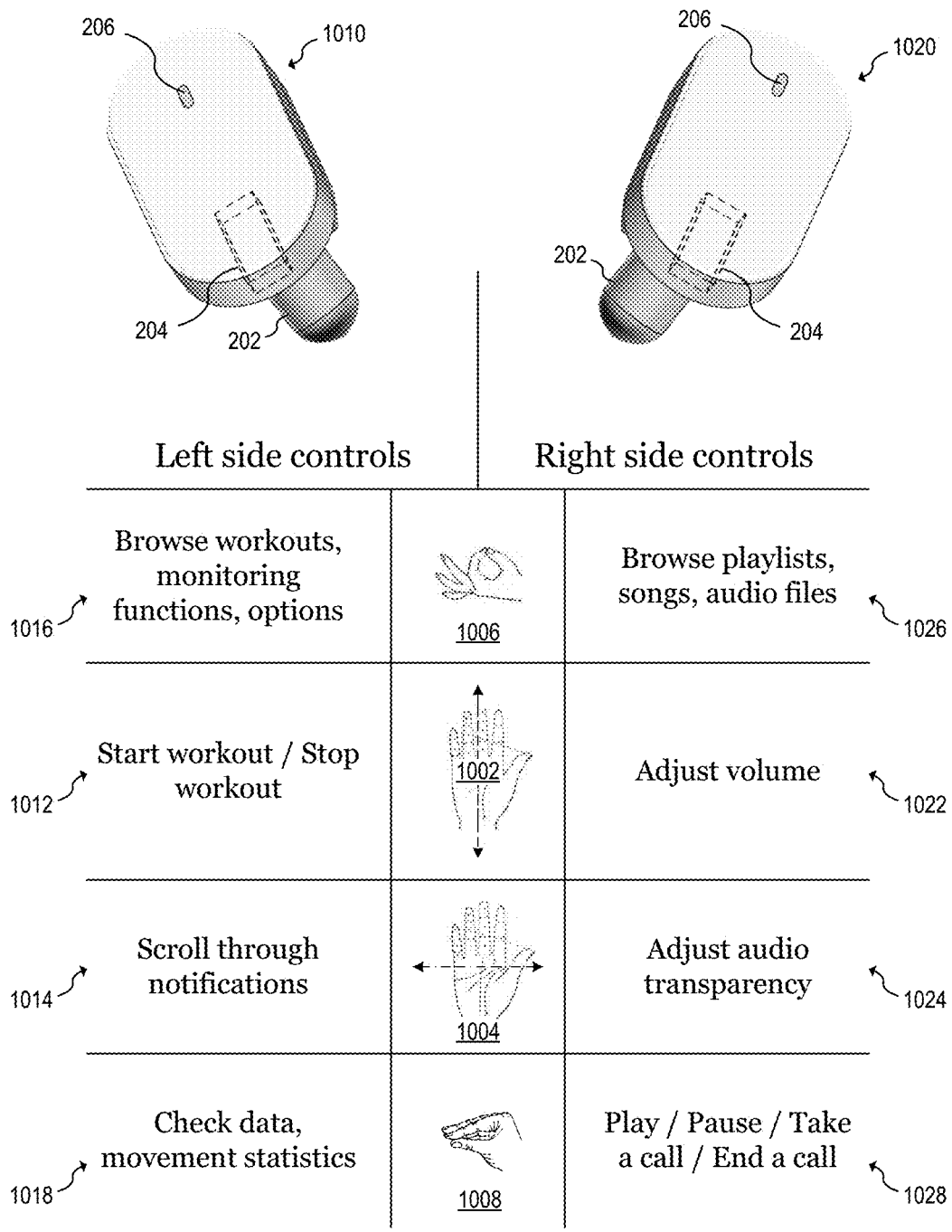
FIG. 10 illustrates example left and right earphones and a table of example gestures and associated functions in accordance with an embodiment of the invention.

FIG. 10 illustrates example left and right earphones and a table of example gestures and associated functions in accordance with an embodiment of the invention. The example left and right earphones may be specific implementations of earphones as previously described in other embodiments such as in reference to FIGS. 1A, 2, 3A, 3B, 7, and 9.

Referring to FIG. 10, an example left earphone low and an example right earphone 1020 each include a radar system 204, acoustic transducer 202, and an optional indicator light 206. All similarly numbered elements are as previously described. Left earphone low and right earphone 1020 may be configured to respond to various gestures as detected by the respective radar systems 204 of the earphones. For example, in one embodiment left earphone low may be configured to recognize a set of gestures as performed by a user's left hand while right earphone 1020 may be configured to recognize a set of gestures as performed by the user's right hand. In another embodiment, the set of gestures is the same for both left earphone low and right earphone 1020.

The set of gestures may include various gestures such as swiping, dragging, selecting, turning, pinching, flicking, closing, opening, or tracing gestures. As shown in FIG. 10, left earphone low and right earphone 1020 may both be configured to detect a vertical swiping gesture 1002, a horizontal swiping gesture 1004, a dragging gesture 1006, and a selecting gesture 1008. In other embodiments, the earphones may be configured to include more or fewer gestures. The earphones may also customizable by a user to include other gestures.

Various functions of the earphones may be controllable using gestures detected by the radar systems 204. For example, the left earphone low may be configured to perform a left side vertical slider function 1012 of starting and/or stopping the recording of data for a workout in response to detecting the vertical swiping gesture 1002. Similarly, left earphone low may also be configured to perform a left side horizontal slider function 1014 of scrolling through notifications in response to detecting the horizontal swiping gesture 1004, perform a left side drag function 1016 of browsing through a first set of menus in response to detecting the dragging gesture 1006, and perform a left side selection function 1018 of checking stored data, movement statistics, and the like in response to detecting the selecting gesture 1008. For example, the pair of earphones including left earphone low may have various menus that may be included in the first set of menus such as stored workouts, monitoring functions, and options that may be browsed and selected using the dragging gesture 1006 and selecting gesture 1008 within the detection range of left earphone low.

The right earphone 1020 may include various right side controls which may be the same or different from the left side controls discussed with respect to left earphone low. For example, instead of starting and/or stopping a workout, right earphone 1020 may be configured to perform a right side vertical slider function 1022 of adjusting the volume in response to detecting the vertical sliding gesture 1002. Similarly, right earphone 1020 may be configured to perform a right side horizontal slider function 1024 of adjusting the audio transparency in response to detecting the horizontal swiping gesture 1004 and perform a right side selection function 1028 of playing audio, pausing audio, taking a call, ending a call, and the like in response to detecting the selecting gesture 1008.

In some cases functionality controlled by the left earphone low and the right earphone 1020 may be similar in response to detecting a similar gesture. For example, like left earphone low, right earphone 1020 may be configured to perform a right side drag function 1026 of browsing a second set of menus in response to detecting a dragging gesture 1006. For example, the pair of earphones including right earphone 1020 may have various menus that may be included in the second set of menus such as playlists, song lists, audio file lists, and others that may be browsed using the dragging gesture 1006 within the detection range of right earphone 1020. Items in the second set of menus may be selected in response to detecting selecting gestures by either the left earphone low or the right earphone 1020.

The gestures and earphone functions described above are merely provided as possible implementations gesture-based control using embodiment radar systems. The number of gestures as well as the type of gestures may be changed to suit the situation. For example, an embodiment radar system may be included in a different type of electronic device requiring different functionality to be associated with each gesture. Similarly, some applications may have many more functions and therefore have many more associated gestures than the four described in conjunction with left earphone low and right earphone 120.

Figure 11:
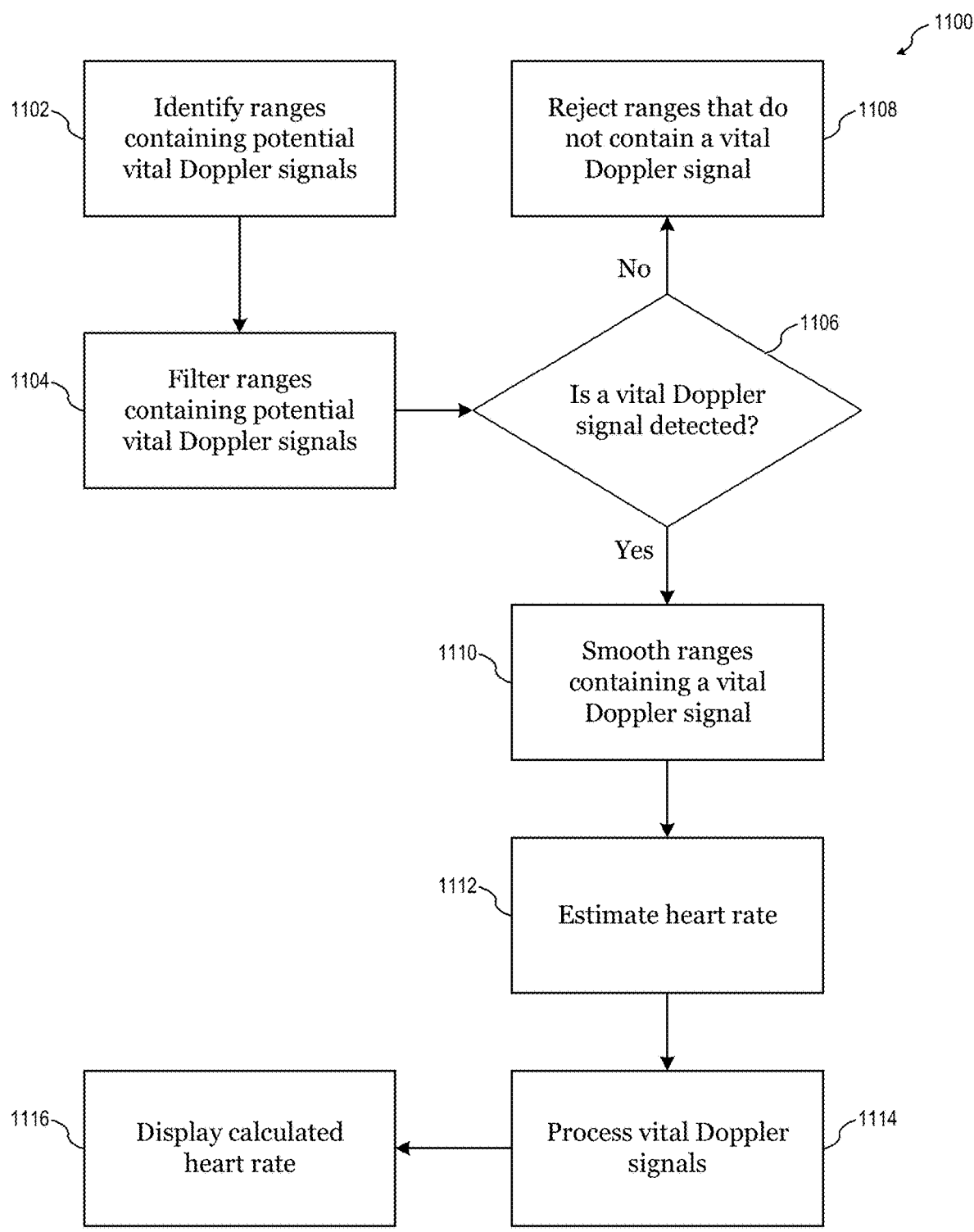
FIG. 11 illustrates an example method of displaying a heart rate according to received reflected RF signals in accordance with an embodiment of the invention.

FIG. 11 illustrates an example method of displaying a heart rate according to received reflected RF signals in accordance with an embodiment of the invention. The method of FIG. 11 may be performed by an embodiment radar system as previously described such as in reference to FIGS. 1A-1D and 2-10.

Referring now to FIG. 11, an example method 1100 is provided in which one or more receive reflected RF signals are processed by a radar system and a heart rate is displayed according to the one or more received reflected RF signals. Received RF signals may, for example, be obtained on a back side of an electronic device that includes an embodiment radar system.

Step 1102 of the method 1100 of displaying a heart rate is identifying ranges in the one or more received RF signals which contain potential vital Doppler signals. For example, various parameters such as mean signal strength, peak-to-average power ratio (PAPR), and the like may be used to determine a period of time in which a potential vital Doppler signal may have been received by the radar system. In various embodiments, the criteria for detecting a potential vital Doppler signal in the one or more received RF signals is determining that a mean signal strength of a signal peak is greater than the signal noise using a predetermined relationship. In one embodiment, the predetermined relationship is that the mean signal strength of a signal peak is greater than twice the noise floor of the RF signal.

In other embodiments, the criteria for detecting a potential vital Doppler signal in the one or more received RF signals is determining that the PAPR is greater than a predetermined value. In one embodiment, a potential vital Doppler signal is detected when the radar system determines that the PAPR is greater than a predetermined value of 1.2 dB. The PAPR may be calculated by squaring the peak amplitude divided by the root-mean-square (RMS) value.

Step 1104 of the method 1100 of displaying a heart rate is filtering ranges which have been identified in step 1102 as containing potential vital Doppler signals. The filtering step 1104 may be used, for example, to isolate the potential vital Doppler signals while removing frequencies that are unlikely to correspond to a user's heart-beat. Various digital filtering methods such as finite impulse response (FIR) filtering or infinite impulse response (IIR) filtering may be used. In one embodiment, the filtering of ranges containing potential vital Doppler signals are centered at a frequency of 0.8 Hz. In one embodiment, the filtering of ranges containing potential vital Doppler signals has a bandwidth of 0.6 Hz. The range of frequencies that are passed through the filter may vary depending on the specific implementation of the heart rate calculation method.

Step 1106 of the method 1100 of displaying a heart rate is to determine if a vital Doppler signal is detected. For each filtered range containing a potential vital Doppler signal, the radar system determines whether a vital Doppler signal is present. If, for a given range, no vital Doppler signal is detected, then that range is rejected in step 1108 and no heart rate corresponding to that range is subsequently displayed. In contrast, all ranges within which a vital Doppler signal is detected are accepted and the method continues with step 1110 of smoothing the accepted ranges. Smoothing the ranges containing vital Doppler signals may reduce the influence of noise due to outside factors unrelated to a user's heart rate.

Step 1112 of the method 1100 of displaying a heart rate is to estimate the heart rate. Heart rate estimation may be useful in order to quickly provide a user with an estimated heart rate. The accuracy of an estimated heart rate may depend on the strength of the vital Doppler signal and sources of noise. Another potential use of heart rate estimation may be to further exempt ranges that contain strong signals and are not associated with a user's heart rate. For example, if the estimated heart rate is outside a predetermined physically possible range, an error may be displayed and the range containing the signals that are not caused by a user's heart rate may be removed prior to continuing to the next step.

Step 1114 of method 1100 of displaying a heart rate is to process the vital Doppler signals in order to obtain a calculated heart rate. The calculated heart rate may have significantly increased accuracy when compared to the estimated heart rate of step 1112. However, processing the vital Doppler signals to obtain a calculated heart rate may take more time than estimating a heart rate. Various processing steps may be implemented in step 1114 such as computing conjunctive weights of the heart rate using a weighting metric. For example, the weighting metric may be the mean or the PAPR of the vital Doppler signal. During step 1114 increased weight may be assigned to certain frequencies. Heart rate frequencies may be centered at around 0.8 Hz and may be in the range of 0.5 Hz to 1.1 Hz, as an example. In this case it may be beneficial to increase the weight of frequencies within the range of 0.5 Hz to 1.1 Hz in order to further distinguish heart rate signals over other signals.

After a calculated heart rate is obtained, the calculate heart rate is displayed in step 1116. In one embodiment, the heart rate is displayed on a screen of the electronic device that includes the radar system. In another embodiment, the heart rate is provided audibly to the user, such as in the case that the electronic device that includes the radar system is an earphone, headphone, headset, or earbud device. In other embodiments, the heart rate is displayed by sending the information to an external device connected to the electronic device that includes the radar system which then displays the heart rate on a screen. For example, the external device may be a smartwatch, mobile phone, tablet, laptop, or desktop computer, etc.

Many of the above described steps of method 1100 may be optional in various implementations. For example, in some embodiments, the filtering step 1104, smoothing step 1106, and/or the estimation step 1112 may be omitted. Additionally, various steps may be combined and/or rearranged depending on the specific implementation of method 1100. In some cases, additional steps may be added at any point in method 1100.

Figure 12:
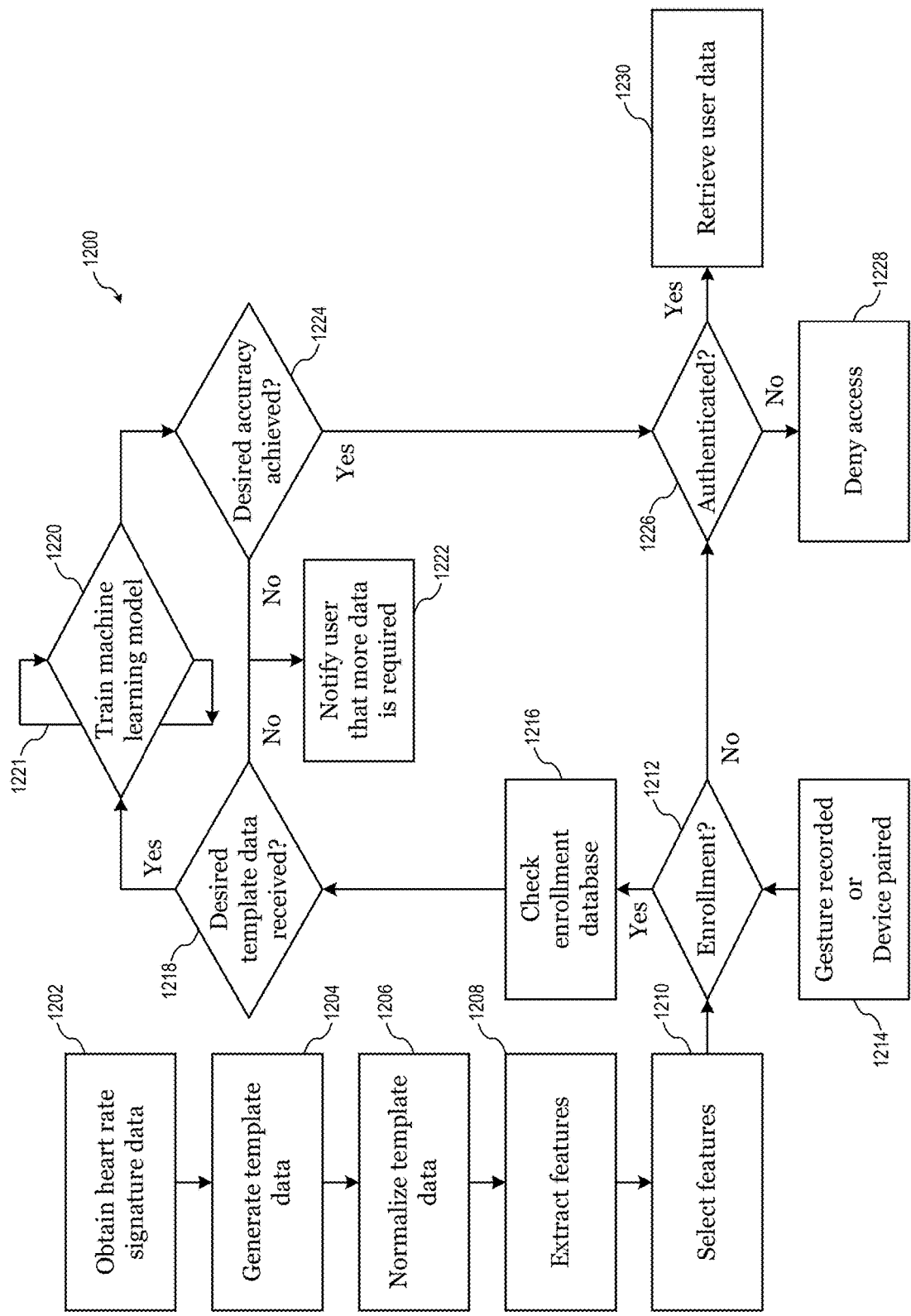
FIG. 12 illustrates an example method of retrieving user data after authentication according to heart rate signature data obtained from received reflected RF signals in accordance with an embodiment of the invention.

FIG. 12 illustrates an example method of retrieving user data after authentication according to heart rate signature data obtained from received reflected RF signals in accordance with an embodiment of the invention. The method of FIG. 12 may be performed by an embodiment radar system as previously described such as in reference to FIGS. 1A-1D and 2-10.

Referring to FIG. 12, an example method 1200 is provided in which heart rate signature data is processed by a radar system in order to enroll a user into the system and/or authenticate a user according to the heart rate signature data and ultimately retrieve user data. Step 1202 of method 1200 is to obtain the heart rate signature data. The heart rate signature data may be obtained, for example, using steps similar to those described in method 1100. In one embodiment, the heart rate signature data may be obtained from step 1106 of method 1100 in which a filtered signal has been determined by the radar system to contain a vital Doppler signal.

Template data may be generated from the heart rate signature data in step 1204. For example, various data points may be obtained from the heart rate signature data. In some cases, it may not be possible to gather all of the data points for the template data for a given heart rate signature. In these cases, these data points may be left blank or at a default value. The template data is then normalized in step 1206. Normalization may or may not always be required depending on the specific implementation of method 1200. Features are then extracted from the template data in step 1208. In step 1210 features of interest are selected from the extracted features. For example, for a given heart rate signature, some features may be more well-defined or may be more useful for authentication and enrollment than other features. These features may be selected in step 1210 while other features may be excluded. In some cases, all extracted features may be selected.

Step 1212 of method 1200 is to determine if the selected features are to be used for enrollment or authentication. For example, a recorded gesture or the pairing of a device in step 1214 may initiate either enrollment or authentication. In one embodiment, the selected features are assumed to be used for authentication as the default unless an appropriate gesture is recorded in step 1214. In another embodiment, the radar system may wait a predetermined amount of time at step 1212 before choosing authentication in the event that no other user events specify enrollment.

If the radar system determines that the selected features obtained from the heart rate signature data are to be used for enrollment, an enrollment database may be checked in step 1216 to determine if the database contains template data corresponding to the selected features obtained in step 1210. In step 1218, the radar system determines whether the desired template data has been received. If the desired template data is not received then the radar system may notify the user in step 1222 that more data is required for enrollment. Alternatively, if the desired template data is received then a machine learning model is used in step 1220 to update the enrollment database in accordance with the selected features of the new heart rate signature data obtained in step 1202. For example, a set of hyper-parameters may be specified as relevant to distinguishing between heart rate signatures of different users. This set of hyper-parameters may include, but is not limited to, average signal strength, discrete cosine transform, maximum likelihood, and others. During steps 1220 and 1221, a machine learning model may use the set of hyper-parameters to categorize the heart rate signature data in the enrollment database.

The step 1220 of training the machine learning model using the new heart rate signature data may be performed iteratively as shown by the step 1221. The machine learning algorithm may dictate when the iterative step 1221 has been completed. After the step 1220 of training the machine learning model has been completed, the radar system may determine whether a desired accuracy has been achieved in step 1224. If the desired accuracy has not been achieved, the radar system may notify the user that more data is required in step 1222. The message to the user at step 1222 may be the same as if step 1222 was reached immediately following step 1218 or it may be different.

If the radar system determines that the desired accuracy is achieved in step 1224, then the radar system may proceed with the step 1226 of authenticating the user. As shown in FIG. 12, the step 1226 may be reached directly from step 1212 from step 1224 after enrollment. The heart rate signature data may be compared to data in the enrollment database using an authentication model to determine if the heart rate signature data belongs to an enrolled user of the electronic device that includes the radar system. If the heart rate data does not match the data of an enrolled user, the radar system may deny access to user-specific data and/or features in step 1228.

In the event that the heart rate signature data is determined to match the data of an enrolled user, authentication is successful in step 1226 and user data is retrieved in step 1230. The user data may include playlists, song history, the last location within a song or audio file, media files, data files, and user settings. For example, an electronic device that includes the radar system may be a pair of earphones. When the earphones are powered on and worn by a user, the radar system in the earphones may obtain a heart rate signature from the user as in step 1202. After the radar system waits a predetermined amount of time in step 1212, and authenticates the user in step 1226, the earphones may retrieve the user's settings, playlist, and location within the current song from cloud storage or local storage. The earphones may then automatically begin playing the last song that the user was listening to with the user's settings such as the volume, audio transparency percentage, equalizer values, etc.

Figure 13:
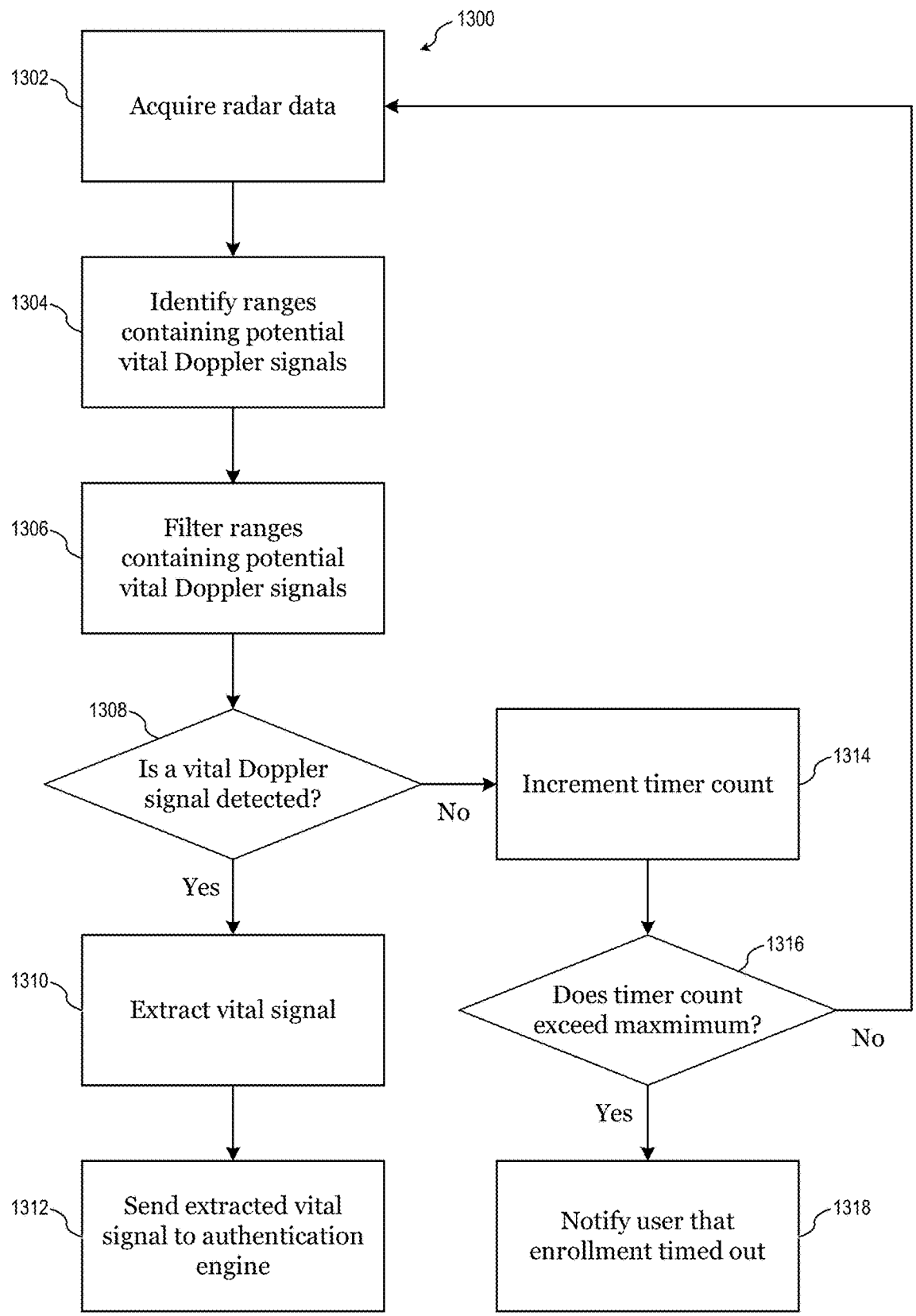
FIG. 13 illustrates an example method of signal extraction for enrollment and authentication according to received radar data in accordance with an embodiment of the invention.

FIG. 13 illustrates an example method of signal extraction for enrollment and authentication according to received radar data in accordance with an embodiment of the invention. The method of FIG. 13 may be performed by an embodiment radar system as previously described such as in reference to FIGS. 1A-1D and 2-10.

Referring to FIG. 13, an example method 1300 is provided in which received radar data is processed by a radar system and extraction of a vital Doppler signal for use in enrollment or authentication. Received radar data may be obtained from one or more received reflected RF signals on a back side of an electronic device that includes an embodiment radar system.

Step 1302 of the method 1300 is acquiring radar data. The radar data may include one or more reflected RF signals measured over a period of time by the radar system. Step 1304 of identifying ranges containing potential vital Doppler signals, step 1306 of filtering the ranges containing potential vital Doppler signals, and step 1308 of determining if a vital Doppler signal is detected may be similar to steps 1102, 1104, and 1106 of method 1100 as previously described.

If a vital Doppler signal is detected in step 1308, then a vital signal may be extracted by the radar system according to the vital Doppler signal in step 1310. For example, step 1310 may include some or all of the steps 1204, 1206, 1208, and 1210 of method 1200 as previously described. After extracting the vital signal in step 1310, the extracted vital signal may be sent to an enrollment and/or authentication engine in step 1312. In various embodiments, step 1312 may be followed by step 1212 or step 1226 of method 1200. For example, the method 1300 may be one way a radar system obtains heart rate signature data for enrollment and/or authentication in the method 1200.

If a vital Doppler signal is not detected in step 1308, a timer count may be incremented in step 1314. The timer function may enable the radar system to determine that the enrollment or authentication process has timed out without a detected a vital signal. The timer may be compared to a predetermined maximum value in step 1316 to determine if an enrollment process has timed out. If the timer count does not exceed the predetermined maximum, the process returns back to step 1302. However, if the timer count exceeds the predetermined maximum, then the method 1300 terminates with the step 1318 of notifying the user than enrollment or authentication timed out.

Figure 14:
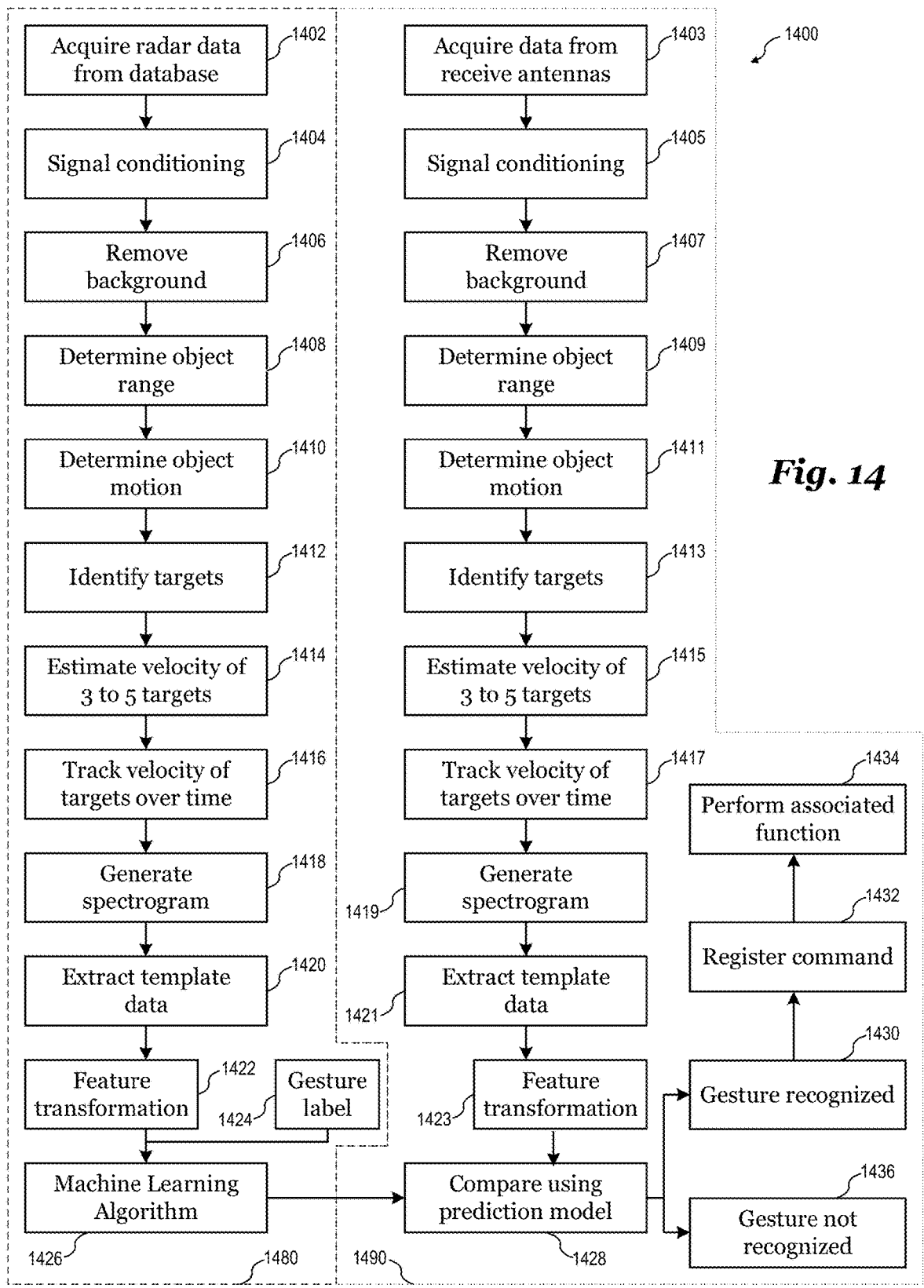
FIG. 14 illustrates an example method of performing a function according to a recognized gesture detected from received reflected RF signals in accordance with an embodiment of the invention.

FIG. 14 illustrates an example method of performing a function according to a recognized gesture detected from received reflected RF signals in accordance with an embodiment of the invention. The method of FIG. 14 may be performed by an embodiment radar system as previously described such as in reference to FIGS. 1A-1D and 2-10.

Referring to FIG. 14, an example method 1400 is provided in which a gesture is recognized by a radar system and a function is performed according to the recognized gesture. The method 1400 is divided into an offline machine learning pipeline 1480 and a live gesture pipeline 1490. The steps of the offline machine learning pipeline 1480 enable the radar system to generate a local database of gestures for use in a prediction model. For example, the steps of the offline machine learning pipeline 1480 may be performed as part of a calibration process for the radar system. The steps of the live gesture pipeline 1490 may be performed to recognize a gesture in real time in order to perform an associated function of the electronic device that includes the radar system.

Step 1402 of the method 1400 is to acquire radar data from a database. The database may be a local database or an external database that stores measured radar data corresponding to various gestures. Step 1403 of acquiring data from receive antennas is similar to step 1402 except that the data is coming directly from measured RF signals received at receive antennas of the radar system. After acquisition of radar data from either a database in step 1402 or the receive antennas in step 1403, both the offline machine learning pipeline 1480 and the live gesture pipeline 1490 perform several similar steps which result in extracted features of interest that may be used to recognize a particular gesture.

Following the offline machine learning pipeline 1480, step 1404 is to condition the radar data to facilitate further processing. Background noise may then be removed in step 1406. The distance that the object generating the radar data is from the radar system, or the object range, is then determined in step 1408 using the radar data. The motion of the object is determined in step 1410. Step 1412 is to identify multiple smaller target surfaces of the object. For example, the multiple smaller targets may include fingers while the object is a user's hand. The velocity of each of the smaller targets is then estimated in step 1414 and then tracked over time in step 1416. The tracking of the velocity of multiple smaller targets, such as fingers, may be used to correlate the movement of the smaller targets with detailed gestures that would not be distinguishable from other gestures without resolving individual finger movement. A spectrogram is generated from the velocity data in step 1418. The spectrogram may contain all the necessary information to describe a gesture as measured by a radar system. Template data is then extracted from the spectrogram in step 1420. The template data may be a summary of the spectrogram in which various representative features are selected. For example, the template data may include features that correspond to specific fingers of a user. The template data is then processed in step 1422 to transform the features into a format that is usable by a machine learning algorithm.

After step 1422, the radar data has been converted into gesture data which may be processed by a machine learning algorithm to learn a gesture. A gesture label may be added to the gesture data in step 1424. In step 1426, a machine learning algorithm may be used by the radar system to categorize and store the gesture data. Stored gesture data may then be referred to by a prediction model in order to allow the radar system to recognize gestures that have been measured in real-time from receive antennas of the radar system as in step 1403, for example.

Now, following the live gesture pipeline 1490, radar data is acquired by the receive antennas of the radar system in step 1403. Similar to the offline machine learning pipeline, a conditioning step 1405, background removal step 1407, object ranging step 1409, object motion step 1411, target identification step 1413, target velocity estimation step 1415, target velocity tracking step 1417, spectrogram generation step 1419, template data extraction step 1421, and feature transformation step 1423 are performed on the radar data to generate live gesture data. The live gesture data is then compared to stored gesture data using a prediction model in step 1428.

It may be determined that the live gesture data corresponds to stored gesture data in step 1430. In this case, the gesture label added to the stored gesture data in step 1424 may be used by the radar system to register an associated command in step 1432. The radar system may then perform an associated function of the electronic device that includes the radar system in step 1434. In some cases the radar system may send the registered command to other components within the electronic device that then perform the associated function. If the live gesture data does not correspond with any stored gesture data, the gesture may not be recognized in step 1436. In this case no command is registered and no associated function is performed.

Example embodiments of the present invention are summarized here. Other embodiments can also be understood from the entirety of the specification as well as the claims filed herein.

Example 1. A radar system including: a substrate including a first side and a second side, the first side being opposite the second side; a first receive antenna disposed at the first side, the first receive antenna being configured to receive a first reflected radio frequency (RF) signal; a second receive antenna configured to receive a second reflected RF signal; and RF circuitry operatively coupled to the first receive antenna and the second receive antenna, the RF circuitry being configured to detect a first object located on the first side of the substrate according to the first reflected RF signal, and detect biometric data from a second object located on the second side of the substrate according to the second reflected RF signal.

Example 2. The radar system of example 1, wherein the radar system is part of an earphone device, a headphone device, a headset device, or an earbud device.

Example 3. The radar system of one of examples 1 and 2, further including a digital signal processor (DSP) operatively coupled to the RF circuitry, the DSP being configured to process signals received from the RF circuitry.

Example 4. The radar system of example 3, wherein the biometric data includes a vital Doppler signal.

Example 5. The radar system of example 4, wherein the DSP is further configured to detect a heart rate according to the vital Doppler signal.

Example 6. The radar system of one of examples 3 to 5, wherein the RF circuitry is further configured to detect motion of the first object, and the DSP is further configured to interpret the motion of the first object as a gesture for controlling the radar system.

Example 7. The radar system of example 6, wherein the radar system is part of an electronic device, wherein the biometric data includes a vital Doppler signal, wherein the DSP is further configured to: detect a heart rate signature according to the vital Doppler signal; authenticate a user by comparing the heart rate signature to stored data; and instruct the electronic device to perform a function associated with the gesture.

Example 8. The radar system of one of examples 1 to 7, further including transmitter front-end circuitry attached to the substrate, the transmitter front-end circuitry being configured to transmit a first transmitted RF signal in a first direction away from the first side, wherein the first reflected RF signal is generated by the first transmitted RF signal, and transmit a second transmitted RF signal in a second direction away from the second side, wherein the second reflected RF signal being generated by the transmitted RF signal.

Example 9. The radar system of one of examples 1 to 8, wherein the second receive antenna is disposed on a flexible substrate, and the flexible substrate is coupled to the substrate and is positioned in close proximity to a source of the biometric data of the second object.

Example 10. A method of operating a radar system, the method including: receiving, by a first receive antenna located at a first side of a substrate, a first reflected radio frequency (RF) signal; detecting, by RF circuitry, a first object located on the first side of the substrate according to the first reflected RF signal, the RF circuitry being operatively coupled to the first receive antenna; receiving, by a second receive antenna operatively coupled to the RF circuitry, a second reflected RF signal; and detecting, by the RF circuitry, biometric data from a second object located on a second side of the substrate according to the second reflected RF signal, wherein the second side is opposite of the first side.

Example 11. The method of example 10, wherein the radar system is an earphone device, a headphone device, a headset device, or an earbud device.

Example 12. The method of one of examples 10 and 11, further including: processing, by a digital signal processor (DSP) operatively coupled to the RF circuitry, signals received from the RF circuitry.

Example 13. The method of example 12, wherein the biometric data includes a vital Doppler signal.

Example 14. The method of example 13, further including: detecting, by the DSP, a heart rate according to the vital Doppler signal.

Example 15. The method of one of examples 12 to 14, further including: detecting, by the RF circuitry, motion of the first object; and interpreting, by the DSP, the motion of the first object as a gesture for controlling the radar system.

Example 16. The method of one of examples 10 to 15, further including: transmitting, by transmitter front-end circuitry, a first transmitted RF signal in a first direction away from the first side, wherein the first reflected RF signal is generated by the first transmitted RF signal; and transmitting, by the transmitted front-end circuitry, a second transmitted RF signal in a second direction away from the second side, wherein the second reflected RF signal being generated by the transmitted RF signal.

Example 17. The method of one of examples 10 to 16, wherein the second receive antenna is disposed on a flexible substrate, and the flexible substrate is coupled to the substrate and is positioned in close proximity to a source of the biometric data of the second object.

Example 18. An earphone device including: a housing including a top region and a bottom region; an acoustic transducer disposed in the bottom region of the housing; and a radar system disposed in the top region of the housing, the radar system including a first side and an opposite second side, wherein the radar system is configured to detect a first object located on the first side of the radar system, and detect biometric data from a second object located on the second side of the radar system.

Example 19. The earphone device of example 18, wherein the biometric data includes a vital Doppler signal, and wherein the radar system includes a digital signal processor and is further configured to: identify a range in the biometric data containing the vital Doppler signal; and calculate a heart rate by processing the vital Doppler signal using the digital signal processor.

Example 20. The earphone device of one of examples 18 and 19, wherein the radar system includes a digital signal processor and is further configured to: detect motion of the first object on the first side of the radar system; interpret the motion of the first object as detected gesture data using the digital signal processor; and recognize the detected gesture data as a gesture by comparing the detected gesture data to stored gesture data, wherein the earphone device is configured to perform a function associated with the gesture.

Example 21. The earphone device of one of examples 18 to 20, wherein the biometric data includes heart rate signature data, and wherein the radar system includes a digital signal processor and is further configured to: extract features from the heart rate signature data using the digital signal processor; determine that the heart rate signature data is from an enrolled user of the earphone device by comparing the extracted features to data in an enrollment database; and retrieving user data associated with the enrolled user.

Example 22. A method of operating an earphone device, the method including: detecting, at a first side of the earphone device, motion of a first object; interpreting the motion of the first object as a gesture; controlling the earphone device according to the gesture; and detecting, at a second side of the earphone device, biometric data of a second object, the second side being opposite the first side.

Example 23. The method of example 22, further including: interpreting the biometric data as heart rate signature data; authenticating the heart rate signature data by matching the heart rate signature data to data in an enrollment database; and retrieving user data associated with the heart rate signature data.

Example 24. The method of example 23, wherein the user data associated with the heart rate signature data includes a setting, playlist, or device history.

Example 25. The method of one of examples 22 to 24, wherein controlling the earphone device according to the gesture includes interpreting the gesture as a swiping gesture, a dragging gesture, or a selecting gesture, and executing an associated function of the earphone device according to the swiping gesture, the dragging gesture, or the selecting gesture.

Example 26. A method of operating an earphone device, the method including: checking an enrollment database for template data; determining that template data has been received from the enrollment database; and updating the enrollment database using heart rate signature data.

Example 27. The method of example 26, further including: determining that template data has not been received; and notifying a user that more data is required.

Example 28. The method of one of examples 26 and 27, further including: iteratively updating the enrollment database using a machine learning model; and determining that a desired accuracy has been achieved after iteratively updating the enrollment database.

Example 29. The method of example 28, further including: determining that the desired accuracy has not been achieved after iteratively updating the enrollment database; and notifying the user that more data is required.

Example 30. The method of one of examples 26 to 29, further including authenticating a user after updating the enrollment database.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:
1. A radar system comprising:
a substrate comprising a first conductive layer at a first side of the substrate and a second conductive layer at a second side of the substrate, the substrate being a circuit board substrate or a wafer substrate, wherein the first side is opposite the second side;
a first receive antenna implemented in the first conductive layer and configured to receive a first reflected radio frequency (RF) signal;
a second receive antenna implemented in the second conductive layer and configured to receive a second reflected RF signal;
a ground plane region implemented in a third conductive layer within the substrate between the first conductive layer and the second conductive layer;
RF circuitry operatively coupled to the first receive antenna and the second receive antenna, the RF circuitry being configured to
detect a first object located on the first side of the substrate according to the first reflected RF signal,
detect motion of the first object, and
detect biometric data from a second object located on the second side of the substrate according to the second reflected RF signal; and
wherein the radar system is configured to interpret the motion of the first object as a gesture for controlling the radar system.

2. The radar system of claim 1, wherein the radar system is part of an earphone device, a headphone device, a headset device, or an earbud device.

3. The radar system of claim 1, further comprising a digital signal processor (DSP) operatively coupled to the RF circuitry, the DSP being configured to process signals received from the RF circuitry and to interpret the motion of the first object as the gesture for controlling the radar system.

4. The radar system of claim 3, wherein the biometric data comprises a vital Doppler signal.

5. The radar system of claim 4, wherein the DSP is further configured to detect a heart rate according to the vital Doppler signal.

6. The radar system of claim 3, wherein the radar system is part of an electronic device, wherein the biometric data comprises a vital Doppler signal, and wherein the DSP is further configured to:

detect a heart rate signature according to the vital Doppler signal;
authenticate a user by comparing the heart rate signature to stored data; and
instruct the electronic device to perform a function associated with the gesture.

7. The radar system of claim 1, further comprising
transmitter front-end circuitry attached to the substrate, the transmitter front-end circuitry being configured to
transmit a first transmitted RF signal in a first direction away from the first side, wherein the first reflected RF signal is generated by the first transmitted RF signal, and
transmit a second transmitted RF signal in a second direction away from the second side, wherein the second reflected RF signal being generated by the second transmitted RF signal.

8. A method of operating a radar system, the method comprising:
receiving, by a first receive antenna implemented in a first conductive layer at a first side of a substrate, a first reflected radio frequency (RF) signal, the substrate being a circuit board substrate or a wafer substrate;
detecting, by RF circuitry, a first object located on the first side of the substrate according to the first reflected RF signal, the RF circuitry being operatively coupled to the first receive antenna;
receiving, by a second receive antenna implemented in a second conductive layer at a second side of the substrate and operatively coupled to the RF circuitry, a second reflected RF signal;
shielding the first receive antenna from the second receive antenna using a ground plane region implemented in a third conductive layer within the substrate between the first conductive layer and the second conductive layer;
detecting, by the RF circuitry, biometric data from a second object located on the second side of the substrate according to the second reflected RF signal, wherein the second side is opposite of the first side;
detecting, by the RF circuitry, motion of the first object; and
interpreting the motion of the first object as a gesture for controlling the radar system.

9. The method of claim 8, wherein the radar system is an earphone device, a headphone device, a headset device, or an earbud device.

10. The method of claim 8, further comprising:
processing, by a digital signal processor (DSP) operatively coupled to the RF circuitry, signals received from the RF circuitry.

11. The method of claim 10, wherein the biometric data comprises a vital Doppler signal.

12. The method of claim 11, further comprising:
detecting, by the DSP, a heart rate according to the vital Doppler signal.

13. The method of claim 10, wherein interpreting the motion of the first object as the gesture for controlling the radar system is performed by the DSP.

14. The method of claim 8, further comprising:
transmitting, by transmitter front-end circuitry, a first transmitted RF signal in a first direction away from the first side, wherein the first reflected RF signal is generated by the first transmitted RF signal; and
transmitting, by the transmitted front-end circuitry, a second transmitted RF signal in a second direction away from the second side, wherein the second reflected RF signal being generated by the second transmitted RF signal.

15. A radar system comprising:
a multilayer circuit board comprising a front side, a first conductive layer disposed within the multilayer circuit board at the front side, a back side opposite the front side, and a second conductive layer disposed within the multilayer circuit board at the back side;
an integrated circuit (IC) chip physically and electrically coupled to the back side of the multilayer circuit board, the IC chip comprising a radar system circuit and a digital signal processor (DSP);
a first receive antenna and a second receive antenna disposed at the front side and configured to receive a first reflected radio frequency (RF) signal, the first receive antenna and second receive antenna being operationally coupled to the radar system circuit and the DSP using transmission lines and interconnects implemented in the second conductive layer;
a flexible substrate comprising a proximal end coupled to the multilayer circuit board;
a third receive antenna disposed at a distal end of the flexible substrate and configured to receive a second reflected RF signal, the flexible substrate extending from the back side and bending so that the distal end including the third receive antenna is spatially separated from and vertically overlaps the back side;
a ground plane region implemented in the first conductive layer and configured to shield the first receive antenna and the second receive antenna from the third receive antenna; and
RF circuitry disposed in the radar system circuit and operatively coupled to the first receive antenna, the second receive antenna, the third receive antenna, and the DSP, the RF circuitry being configured to
detect a first object located on the front side of the multilayer circuit board according to the first reflected RF signal, and
detect biometric data from a second object located on the back side of the multilayer circuit board according to the second reflected RF signal.

16. The radar system of claim 15, wherein the radar system is part of an earphone device, a headphone device, a headset device, or an earbud device.

17. The radar system of claim 15, wherein:
the RF circuitry is further configured to detect motion of the first object; and
the DSP is configured to process signals received from the RF circuitry and to interpret the motion of the first object as a gesture for controlling the radar system.

18. The radar system of claim 17, wherein the radar system is part of an electronic device, wherein the biometric data comprises a vital Doppler signal, wherein the DSP is further configured to:
detect a heart rate signature according to the vital Doppler signal;
authenticate a user by comparing the heart rate signature to stored data; and
instruct the electronic device to perform a function associated with the gesture.

19. The radar system of claim 15, wherein the DSP is configured to process signals received from the RF circuitry.

20. The radar system of claim 19, wherein the biometric data comprises a vital Doppler signal.

21. A method of operating a radar system, the method comprising:

receiving, by a first receive antenna implemented in a first conductive layer at a first side of a substrate, a first reflected radio frequency (RF) signal, the substrate being a circuit board substrate or a wafer substrate;

detecting, by RF circuitry, a first object located on the first side of the substrate according to the first reflected RF signal, the RF circuitry being operatively coupled to the first receive antenna;

receiving, by a second receive antenna implemented in a second conductive layer at a second side of the substrate and operatively coupled to the RF circuitry, a second reflected RF signal;

shielding the first receive antenna from the second receive antenna using a ground plane region implemented in a third conductive layer within the substrate between the first conductive layer and the second conductive layer;

detecting, by the RF circuitry, biometric data from a second object located on the second side of the substrate according to the second reflected RF signal, wherein the second side is opposite of the first side; and wherein the radar system is an earphone device, a headphone device, a headset device, or an earbud device.

* * * * *